(12) United States Patent
Miraki

(10) Patent No.: US 12,144,499 B2
(45) Date of Patent: Nov. 19, 2024

(54) SUTURE FASTENER HAVING SPACED-APART LAYERS

(71) Applicant: EDWARDS LIFESCIENCES CORPORATION, Irvine, CA (US)

(72) Inventor: Manouchehr A. Miraki, Laguna Hills, CA (US)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 0 days.

(21) Appl. No.: 18/535,985

(22) Filed: Dec. 11, 2023

(65) Prior Publication Data

US 2024/0099712 A1 Mar. 28, 2024

Related U.S. Application Data

(63) Continuation of application No. 17/119,924, filed on Dec. 11, 2020, now Pat. No. 11,957,332, which is a
(Continued)

(51) Int. Cl.
*A61B 17/04* (2006.01)
*A61F 2/24* (2006.01)
*A61B 17/00* (2006.01)

(52) U.S. Cl.
CPC ...... *A61B 17/0487* (2013.01); *A61B 17/0467* (2013.01); *A61B 17/0469* (2013.01);
(Continued)

(58) Field of Classification Search
CPC ............ A61B 17/0401; A61B 17/0467; A61B 17/0469; A61B 17/0487;
(Continued)

(56) References Cited

U.S. PATENT DOCUMENTS 2,264,679 A 12/1941 Ravel
2,516,710 A 7/1950 Mascolo
(Continued)

FOREIGN PATENT DOCUMENTS

CA 2141911 4/2002
CA 2141913 4/2002
(Continued)

OTHER PUBLICATIONS

CN Office Action for App No. 2012800690769, Mar. 23, 2015.
(Continued)

*Primary Examiner* — Kankindi Rwego
(74) *Attorney, Agent, or Firm* — KLARQUIST SPARKMAN, LLP

(57) ABSTRACT

In one embodiment, a multi-layer suture fastener that includes a generally disc-shaped body defining a plurality of axially spaced-apart layers. Each layer can include an inner axial surface and an outer axial surface. A suture opening can extend from the inner axial surface to the outer axial surface of each layer. The suture openings can have an open configuration and a closed configuration. One or more lines of suture can be passed through the suture openings when in the open configuration. The suture openings can be placed in the closed configuration. In the closed configuration, the one or more lines of suture can be restricted by radial surfaces of the suture opening from sliding through the suture openings in at least one longitudinal direction of the one or more lines of suture.

20 Claims, 16 Drawing Sheets

Related U.S. Application Data continuation of application No. 15/847,690, filed on Dec. 19, 2017, now Pat. No. 10,863,980.

(60) Provisional application No. 62/439,868, filed on Dec. 28, 2016.

(52) U.S. Cl.
CPC .......... *A61F 2/2409* (2013.01); *A61F 2/2448* (2013.01); *A61B 2017/00243* (2013.01); *A61B 2017/0488* (2013.01)

(58) Field of Classification Search
CPC .... A61B 2017/0404; A61B 2017/0406; A61B 2017/0438; A61B 2017/0462; A61B 2017/0488; A61B 2017/049; F16G 11/00; F16G 11/02; F16G 11/025; F16G 11/03; F16G 11/04; F16G 11/10; F16G 11/101; F16G 11/103; F16G 11/105; F16G 11/106; Y10T 24/155; Y10T 24/44923; B65D 33/1625; B65D 33/1641
USPC ........................................................ 606/232
See application file for complete search history.

(56) References Cited

U.S. PATENT DOCUMENTS

| | | | |
|---|---|---|---|
| 2,715,486 A | 8/1955 | Marcoff-Moghadam et al. |
| 2,890,519 A | 6/1959 | Storz, Jr. |
| 3,143,742 A | 8/1964 | Cromie |
| 3,249,104 A | 5/1966 | Hohnstein |
| 3,274,658 A | 9/1966 | Pile |
| 3,452,742 A | 7/1969 | Muller |
| 3,506,012 A | 4/1970 | Brown |
| 3,509,882 A | 5/1970 | Blake |
| 3,541,591 A | 11/1970 | Hoegerman |
| 3,547,103 A | 12/1970 | Cook |
| 3,570,497 A | 3/1971 | Lemole |
| 3,608,095 A | 9/1971 | Barry |
| 3,638,654 A | 2/1972 | Akuba |
| RE27,391 E | 6/1972 | Merser |
| 3,753,438 A | 8/1973 | Wood et al. |
| 3,859,668 A | 1/1975 | Anderson |
| 3,875,648 A | 4/1975 | Bone |
| 3,898,999 A | 8/1975 | Haller |
| 3,910,281 A | 10/1975 | Kletschka et al. |
| 3,954,109 A | 5/1976 | Patel |
| 3,958,576 A | 5/1976 | Komiya |
| 3,976,079 A | 8/1976 | Samuels et al. |
| 3,988,810 A | 11/1976 | Emery |
| 3,996,623 A | 12/1976 | Kaster |
| 4,038,725 A | 8/1977 | Keefe |
| 4,103,690 A | 8/1978 | Harris |
| 4,140,125 A | 2/1979 | Smith |
| 4,170,990 A | 10/1979 | Baumgart et al. |
| 4,192,315 A | 3/1980 | Hilzinger et al. |
| 4,217,902 A | 8/1980 | March |
| 4,324,248 A | 4/1982 | Perlin |
| 4,345,601 A | 8/1982 | Fukuda |
| 4,416,266 A | 11/1983 | Baucom |
| 4,456,017 A | 6/1984 | Miles |
| 4,485,816 A | 12/1984 | Krumme |
| 4,522,207 A | 6/1985 | Klieman et al. |
| 4,535,764 A | 8/1985 | Ebert |
| 4,548,202 A | 10/1985 | Duncan |
| 4,549,545 A | 10/1985 | Levy |
| 4,586,502 A | 5/1986 | Bedi et al. |
| 4,586,503 A | 5/1986 | Kirsch et al. |
| 4,595,007 A | 6/1986 | Mericle |
| 4,612,932 A | 9/1986 | Caspar et al. |
| 4,637,380 A | 1/1987 | Orejola |
| 4,665,906 A | 5/1987 | Jervis |
| 4,683,895 A | 8/1987 | Pohndorf |
| 4,705,040 A | 11/1987 | Mueller et al. |
| 4,719,924 A | 1/1988 | Crittenden et al. |
| 4,730,615 A | 3/1988 | Sutherland et al. |
| 4,741,330 A | 5/1988 | Hayhurst |
| 4,743,253 A | 5/1988 | Magladry |
| 4,750,492 A | 6/1988 | Jacobs |
| 4,809,695 A | 3/1989 | Gwathmey et al. |
| 4,823,794 A | 4/1989 | Pierce |
| 4,863,460 A | 9/1989 | Magladry |
| 4,873,975 A | 10/1989 | Walsh et al. |
| 4,896,668 A | 1/1990 | Popoff et al. |
| 4,899,744 A | 2/1990 | Fujitsuka et al. |
| 4,901,721 A | 2/1990 | Hakki |
| 4,924,866 A | 5/1990 | Yoon |
| 4,926,860 A | 5/1990 | Stice et al. |
| 4,929,240 A | 5/1990 | Kirsch et al. |
| 4,932,955 A | 6/1990 | Merz et al. |
| 4,950,283 A | 8/1990 | Dzubow et al. |
| 4,950,285 A | 8/1990 | Wilk |
| 4,955,913 A | 9/1990 | Robinson |
| 4,976,715 A | 12/1990 | Bays et al. |
| 4,983,176 A | 1/1991 | Cushman et al. |
| 4,990,152 A | 2/1991 | Yoon |
| 4,997,439 A | 3/1991 | Chen |
| 5,002,550 A | 3/1991 | Li |
| 5,002,562 A | 3/1991 | Oberlander |
| 5,002,563 A | 3/1991 | Pyka et al. |
| 5,026,379 A | 6/1991 | Yoon |
| 5,047,047 A | 9/1991 | Yoon |
| 5,053,047 A | 10/1991 | Yoon |
| 5,070,805 A | 12/1991 | Plante |
| 5,071,431 A | 12/1991 | Sauter et al. |
| 5,074,874 A | 12/1991 | Yoon et al. |
| 5,078,731 A | 1/1992 | Hayhurst |
| 5,100,418 A | 3/1992 | Yoon et al. |
| 5,116,840 A | 5/1992 | Ganguly et al. |
| 5,123,913 A | 6/1992 | Wilk et al. |
| RE34,021 E | 8/1992 | Mueller et al. |
| 5,152,769 A | 10/1992 | Baber |
| 5,154,189 A | 10/1992 | Oberlander |
| 5,158,566 A | 10/1992 | Pianetti |
| 5,163,954 A | 11/1992 | Curcio et al. |
| 5,171,250 A | 12/1992 | Yoon |
| 5,171,251 A | 12/1992 | Bregen et al. |
| 5,171,252 A | 12/1992 | Friedland |
| 5,174,087 A | 12/1992 | Bruno |
| 5,196,022 A | 3/1993 | Bilweis |
| 5,219,358 A | 6/1993 | Bendel et al. |
| 5,222,976 A | 6/1993 | Yoon |
| 5,234,449 A | 8/1993 | Bruker et al. |
| 5,236,440 A | 8/1993 | Hlavacek |
| 5,242,456 A | 9/1993 | Nash et al. |
| 5,246,443 A | 9/1993 | Mai |
| 5,258,011 A | 11/1993 | Drews |
| 5,258,015 A | 11/1993 | Li et al. |
| 5,269,783 A | 12/1993 | Sander |
| 5,269,809 A | 12/1993 | Hayhurst et al. |
| 5,282,832 A | 2/1994 | Toso et al. |
| 5,290,289 A | 3/1994 | Sanders et al. |
| 5,304,204 A | 4/1994 | Bregen |
| 5,306,290 A | 4/1994 | Martins et al. |
| 5,306,296 A | 4/1994 | Wright et al. |
| 5,312,436 A | 5/1994 | Coffey et al. |
| 5,330,503 A | 7/1994 | Yoon |
| 5,336,239 A | 8/1994 | Gimpelson |
| 5,356,424 A | 10/1994 | Buzerak et al. |
| 5,374,268 A | 12/1994 | Sander |
| 5,383,904 A | 1/1995 | Totakura et al. |
| 5,383,905 A | 1/1995 | Golds et al. |
| 5,391,173 A | 2/1995 | Wilk |
| 5,403,346 A | 4/1995 | Loeser |
| 5,409,499 A | 4/1995 | Yi |
| 5,437,680 A | 8/1995 | Yoon |
| 5,437,685 A | 8/1995 | Blasnik |
| 5,439,479 A | 8/1995 | Shichman et al. |
| 5,445,167 A | 8/1995 | Yoon et al. |
| 5,450,860 A | 9/1995 | O'Connor |
| 5,452,733 A | 9/1995 | Sterman et al. |
| 5,456,246 A | 10/1995 | Schmieding et al. |
| 5,462,558 A | 10/1995 | Kolesa et al. |

(56) References Cited

U.S. PATENT DOCUMENTS

| | | |
|---|---|---|
| 5,462,561 A | 10/1995 | Voda |
| 5,474,557 A | 12/1995 | Mai |
| 5,474,572 A | 12/1995 | Hayhurst |
| 5,480,405 A | 1/1996 | Yoon |
| 5,486,197 A | 1/1996 | Le et al. |
| 5,496,336 A | 3/1996 | Cosgrove et al. |
| 5,499,990 A | 3/1996 | Schulken et al. |
| 5,500,000 A | 3/1996 | Feagin et al. |
| 5,520,691 A | 5/1996 | Branch |
| 5,520,702 A | 5/1996 | Sauer et al. |
| 5,527,342 A | 6/1996 | Pietrzak et al. |
| 5,531,763 A | 7/1996 | Mastri et al. |
| 5,545,178 A | 8/1996 | Kensey et al. |
| 5,549,619 A | 8/1996 | Peters et al. |
| 5,562,685 A | 10/1996 | Mollenauer et al. |
| 5,569,274 A | 10/1996 | Rapacki et al. |
| 5,569,301 A | 10/1996 | Granger et al. |
| 5,582,616 A | 12/1996 | Bolduc et al. |
| 5,582,619 A | 12/1996 | Ken |
| 5,586,983 A | 12/1996 | Sanders et al. |
| 5,591,179 A | 1/1997 | Edelstein |
| 5,593,414 A | 1/1997 | Shipp et al. |
| 5,593,424 A | 1/1997 | Northrup, III |
| 5,609,608 A | 3/1997 | Benett et al. |
| 5,626,590 A | 5/1997 | Wilk |
| 5,630,824 A | 5/1997 | Hart |
| 5,632,752 A | 5/1997 | Buelna |
| 5,632,753 A | 5/1997 | Loeser |
| 5,643,289 A | 7/1997 | Sauer et al. |
| 5,643,295 A | 7/1997 | Yoon |
| 5,645,553 A | 7/1997 | Kolesa et al. |
| 5,645,568 A | 7/1997 | Chervitz et al. |
| 5,665,109 A | 9/1997 | Yoon |
| 5,669,917 A | 9/1997 | Sauer et al. |
| 5,669,935 A | 9/1997 | Rosenman et al. |
| 5,681,351 A | 10/1997 | Jamiolkowski et al. |
| 5,683,417 A | 11/1997 | Cooper |
| 5,695,505 A | 12/1997 | Yoon |
| 5,697,943 A | 12/1997 | Sauer et al. |
| 5,700,270 A | 12/1997 | Peyser et al. |
| 5,700,271 A | 12/1997 | Whitfield et al. |
| 5,707,380 A | 1/1998 | Hinchliffe et al. |
| 5,709,693 A | 1/1998 | Taylor |
| 5,709,695 A | 1/1998 | Northrup |
| 5,725,539 A | 3/1998 | Matern |
| 5,725,542 A | 3/1998 | Yoon |
| 5,725,556 A | 3/1998 | Moser et al. |
| 5,728,135 A | 3/1998 | Bregen et al. |
| 5,735,290 A | 4/1998 | Sterman et al. |
| 5,735,877 A | 4/1998 | Pagedas |
| 5,766,183 A | 6/1998 | Sauer |
| 5,776,188 A | 7/1998 | Shepherd et al. |
| 5,799,661 A | 9/1998 | Boyd et al. |
| 5,810,851 A | 9/1998 | Yoon |
| 5,810,882 A | 9/1998 | Bolduc et al. |
| 5,820,631 A | 10/1998 | Nobles |
| 5,824,008 A | 10/1998 | Bolduc et al. |
| 5,830,221 A | 11/1998 | Stein et al. |
| 5,833,696 A | 11/1998 | Whitfield et al. |
| 5,845,645 A | 12/1998 | Bonutti |
| 5,849,019 A | 12/1998 | Yoon |
| 5,861,004 A | 1/1999 | Kensey et al. |
| 5,879,371 A | 3/1999 | Gardiner et al. |
| 5,891,130 A | 4/1999 | Palermo et al. |
| 5,891,160 A | 4/1999 | Williamson, IV et al. |
| 5,895,393 A | 4/1999 | Pagedas |
| 5,895,394 A | 4/1999 | Kienzle et al. |
| 5,919,207 A | 7/1999 | Taheri |
| 5,948,001 A | 9/1999 | Larsen |
| 5,961,481 A | 10/1999 | Sterman et al. |
| 5,961,539 A | 10/1999 | Northrup, III et al. |
| 5,964,772 A | 10/1999 | Bolduc et al. |
| 5,972,024 A | 10/1999 | Northrup, III et al. |
| 5,976,159 A | 11/1999 | Bolduc et al. |
| 5,984,917 A | 11/1999 | Fleischman et al. |
| 5,989,242 A | 11/1999 | Saadat et al. |
| 5,989,268 A | 11/1999 | Pugsley, Jr. et al. |
| 5,997,556 A | 12/1999 | Tanner |
| 6,001,110 A | 12/1999 | Adams |
| 6,013,084 A | 1/2000 | Ken et al. |
| 6,015,428 A | 1/2000 | Pagedas |
| 6,039,176 A | 3/2000 | Wright |
| 6,066,160 A | 5/2000 | Colvin et al. |
| 6,074,409 A | 6/2000 | Goldfarb |
| 6,120,524 A | 9/2000 | Taheri |
| 6,132,438 A | 10/2000 | Fleischman et al. |
| 6,139,540 A | 10/2000 | Rost et al. |
| 6,143,004 A | 11/2000 | Davis et al. |
| 6,176,413 B1 | 1/2001 | Heck et al. |
| 6,190,373 B1 | 2/2001 | Palermo et al. |
| 6,193,733 B1 | 2/2001 | Adams |
| 6,193,734 B1 | 2/2001 | Bolduc et al. |
| 6,231,592 B1 | 5/2001 | Bonutti et al. |
| 6,241,765 B1 | 6/2001 | Griffin et al. |
| 6,254,615 B1 | 7/2001 | Bolduc et al. |
| 6,293,961 B2 | 9/2001 | Schwartz et al. |
| 6,306,141 B1 | 10/2001 | Jervis |
| 6,346,112 B2 | 2/2002 | Adams |
| 6,368,334 B1 | 4/2002 | Sauer |
| 6,432,123 B2 | 8/2002 | Schwartz et al. |
| 6,475,230 B1 | 11/2002 | Bonutti et al. |
| 6,514,265 B2 | 2/2003 | Ho et al. |
| 6,533,796 B1 | 3/2003 | Sauer et al. |
| 6,537,290 B2 | 3/2003 | Adams et al. |
| 6,551,332 B1 | 4/2003 | Nguyen et al. |
| 6,589,279 B1 | 7/2003 | Anderson et al. |
| 6,607,541 B1 | 8/2003 | Gardiner et al. |
| 6,613,059 B2 | 9/2003 | Schaller et al. |
| 6,626,930 B1 | 9/2003 | Allen et al. |
| 6,641,592 B1 | 11/2003 | Sauer et al. |
| 6,641,593 B1 | 11/2003 | Schaller et al. |
| 6,682,540 B1 | 1/2004 | Sancoff et al. |
| 6,719,767 B1 | 4/2004 | Kimblad |
| 6,746,457 B2 | 6/2004 | Dana et al. |
| 6,749,622 B2 | 6/2004 | McGuckin, Jr. et al. |
| 6,776,784 B2 | 8/2004 | Ginn |
| 6,860,890 B2 | 3/2005 | Bachman et al. |
| 6,896,686 B2 | 5/2005 | Weber |
| 6,913,607 B2 | 7/2005 | Ainsworth et al. |
| 6,918,917 B1 | 7/2005 | Nguyen et al. |
| 6,921,407 B2 | 7/2005 | Nguyen et al. |
| 6,926,730 B1 | 8/2005 | Nguyen et al. |
| 6,945,980 B2 | 9/2005 | Nguyen et al. |
| 6,960,221 B2 | 11/2005 | Ho et al. |
| 7,011,669 B2 | 3/2006 | Kimblad |
| 7,083,628 B2 | 8/2006 | Bachman |
| 7,094,244 B2 | 8/2006 | Schreck |
| 7,112,207 B2 | 9/2006 | Allen et al. |
| 7,220,266 B2 | 5/2007 | Gambale |
| 7,235,086 B2 | 6/2007 | Sauer et al. |
| 7,264,625 B1 | 9/2007 | Buncke |
| 7,381,210 B2 | 6/2008 | Zarbatany et al. |
| 7,628,797 B2 | 12/2009 | Tieu et al. |
| 7,731,727 B2 | 6/2010 | Sauer |
| 7,833,237 B2 | 11/2010 | Sauer |
| 7,842,051 B2 | 11/2010 | Dana et al. |
| 7,862,584 B2 | 1/2011 | Lyons et al. |
| 7,875,056 B2 | 1/2011 | Jervis et al. |
| 7,959,674 B2 | 6/2011 | Shu et al. |
| 7,981,139 B2 | 7/2011 | Martin et al. |
| 8,021,421 B2 | 9/2011 | Fogarty et al. |
| 8,100,923 B2 | 1/2012 | Paraschac et al. |
| 8,105,355 B2 | 1/2012 | Page et al. |
| 8,252,005 B2 | 8/2012 | Findlay, III et al. |
| 8,398,657 B2 | 3/2013 | Sauer |
| 8,398,680 B2 | 3/2013 | Sauer et al. |
| 8,425,555 B2 | 4/2013 | Page et al. |
| 8,480,686 B2 | 7/2013 | Bakos et al. |
| 8,753,373 B2 | 6/2014 | Chau et al. |
| 9,017,347 B2 | 4/2015 | Oba et al. |
| 9,393,008 B2 | 7/2016 | Stanley |
| 9,498,202 B2 | 11/2016 | Jafari et al. |
| 2003/0109922 A1 | 6/2003 | Peterson et al. |
| 2003/0195563 A1 | 10/2003 | Foerster |

(56) References Cited

U.S. PATENT DOCUMENTS

| | | |
|---|---|---|
| 2003/0233105 A1 | 12/2003 | Gayton |
| 2004/0102809 A1* | 5/2004 | Anderson .......... A61B 17/0487 606/232 |
| 2004/0181238 A1 | 9/2004 | Zarbatany et al. |
| 2004/0204724 A1 | 10/2004 | Kissel et al. |
| 2004/0249414 A1 | 12/2004 | Kissel et al. |
| 2005/0251209 A1 | 11/2005 | Saadat et al. |
| 2006/0047314 A1 | 3/2006 | Green |
| 2006/0079913 A1 | 4/2006 | Whitfield et al. |
| 2006/0089571 A1 | 4/2006 | Gertner |
| 2006/0184203 A1 | 8/2006 | Martin et al. |
| 2006/0265010 A1 | 11/2006 | Paraschac et al. |
| 2006/0265012 A1 | 11/2006 | Anderson |
| 2006/0276871 A1 | 12/2006 | Lamson et al. |
| 2006/0282119 A1 | 12/2006 | Perchik |
| 2007/0005079 A1 | 1/2007 | Zarbatany et al. |
| 2007/0005081 A1 | 1/2007 | Findlay et al. |
| 2007/0049952 A1 | 3/2007 | Weiss |
| 2007/0049970 A1 | 3/2007 | Belef et al. |
| 2007/0088391 A1 | 4/2007 | McAlexander et al. |
| 2007/0179530 A1 | 8/2007 | Tieu et al. |
| 2007/0270907 A1 | 11/2007 | Stokes et al. |
| 2008/0154286 A1 | 6/2008 | Abbott et al. |
| 2008/0255591 A1 | 10/2008 | Harada et al. |
| 2008/0281356 A1 | 11/2008 | Chau et al. |
| 2009/0143821 A1 | 6/2009 | Stupak |
| 2009/0281377 A1 | 11/2009 | Newell et al. |
| 2010/0001038 A1 | 1/2010 | Levin et al. |
| 2010/0076462 A1 | 3/2010 | Bakos et al. |
| 2010/0324597 A1 | 12/2010 | Shikhman |
| 2011/0087241 A1 | 4/2011 | Nguyen |
| 2011/0087242 A1 | 4/2011 | Pribanic et al. |
| 2011/0224714 A1 | 9/2011 | Gertner |
| 2011/0283514 A1 | 11/2011 | Fogarty et al. |
| 2012/0089182 A1 | 4/2012 | Page et al. |
| 2012/0102526 A1 | 4/2012 | Lejeune |
| 2013/0053884 A1 | 2/2013 | Roorda |
| 2013/0110164 A1 | 5/2013 | Milazzo et al. |
| 2013/0158600 A1 | 6/2013 | Conklin et al. |
| 2013/0165953 A1 | 6/2013 | Oba et al. |
| 2013/0204297 A1 | 8/2013 | Melsheimer et al. |
| 2013/0282028 A1 | 10/2013 | Conklin et al. |
| 2014/0031864 A1 | 1/2014 | Jafari et al. |

FOREIGN PATENT DOCUMENTS

| | | |
|---|---|---|
| CN | 2558335 Y | 7/2003 |
| CN | 105073026 A | 11/2015 |
| DE | 69512446 T2 | 5/2000 |
| DE | 69612447 T2 | 7/2001 |
| EP | 0669101 A1 | 8/1995 |
| EP | 0669103 A1 | 8/1995 |
| EP | 1484023 A1 | 12/2004 |
| WO | 0030550 A1 | 6/2000 |
| WO | 01049207 A2 | 7/2001 |
| WO | 0166001 A2 | 9/2001 |
| WO | 2004/024006 A1 | 3/2004 |

OTHER PUBLICATIONS

EP Supplementary European Search Report issued for EP14823055, dated Jan. 10, 2017.
EP Supplementary Search Report for EP12858766, completed Sep. 7, 2015.
European Search Report issued for Application No. 12858766.4, Sep. 16, 2015.
European Supplementary Search Report issued Feb. 9, 2016 for EP13817447.
Int'l. Search Report for PCT/US15/65033, mailed Feb. 18, 2016.
Int'l. Search Report for PCT/US2016/022495, mailed Jun. 1, 2016.
International Search Report for PCT/US2014/046423, Oct. 20, 2014.
Office Action for CN 2013800370375, issued Mar. 28, 2016.

* cited by examiner

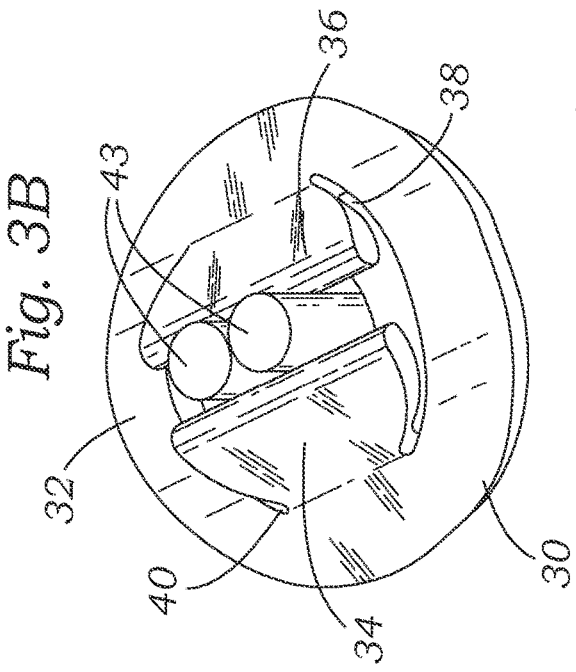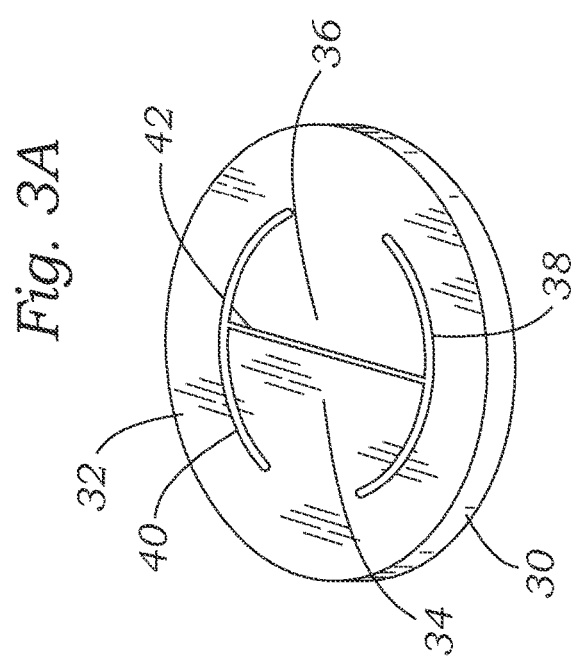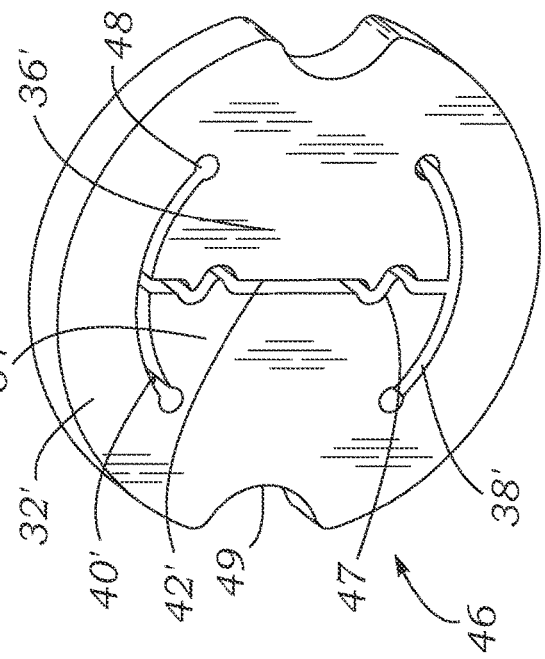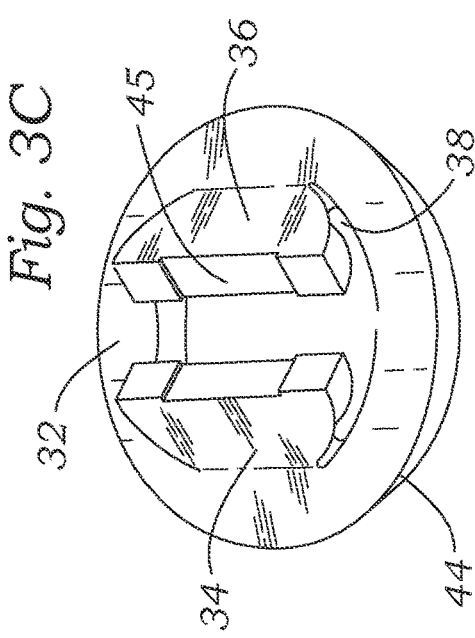

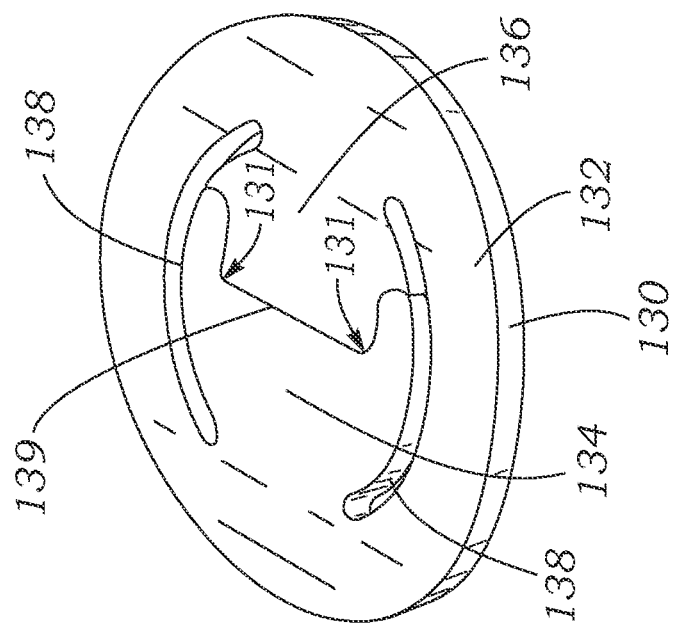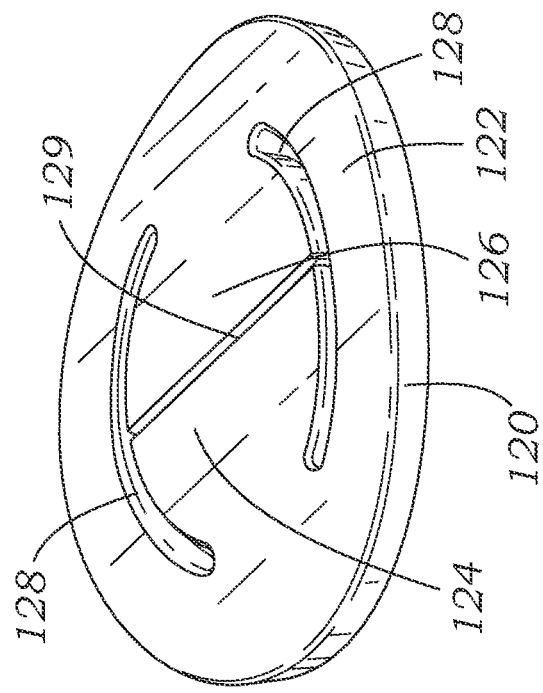

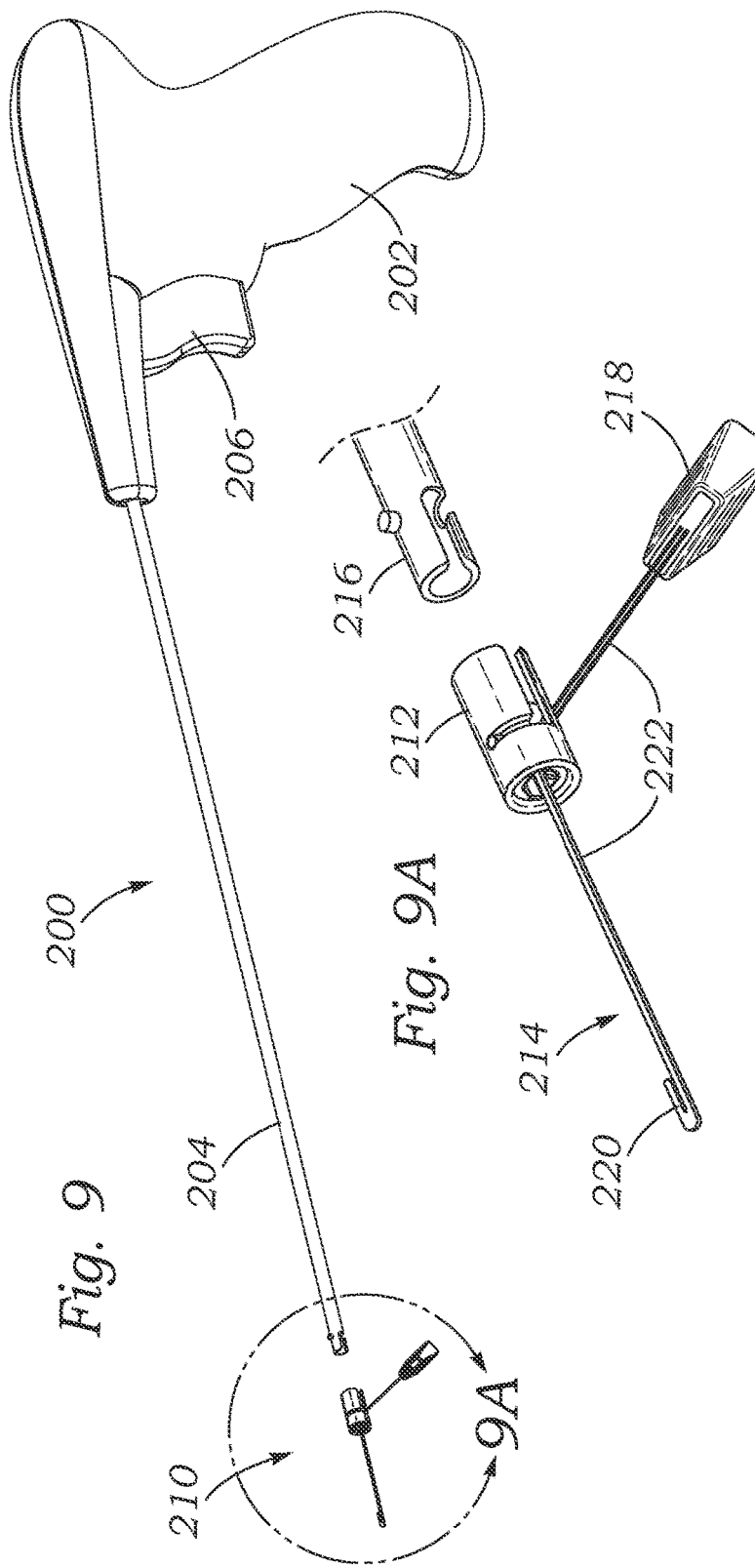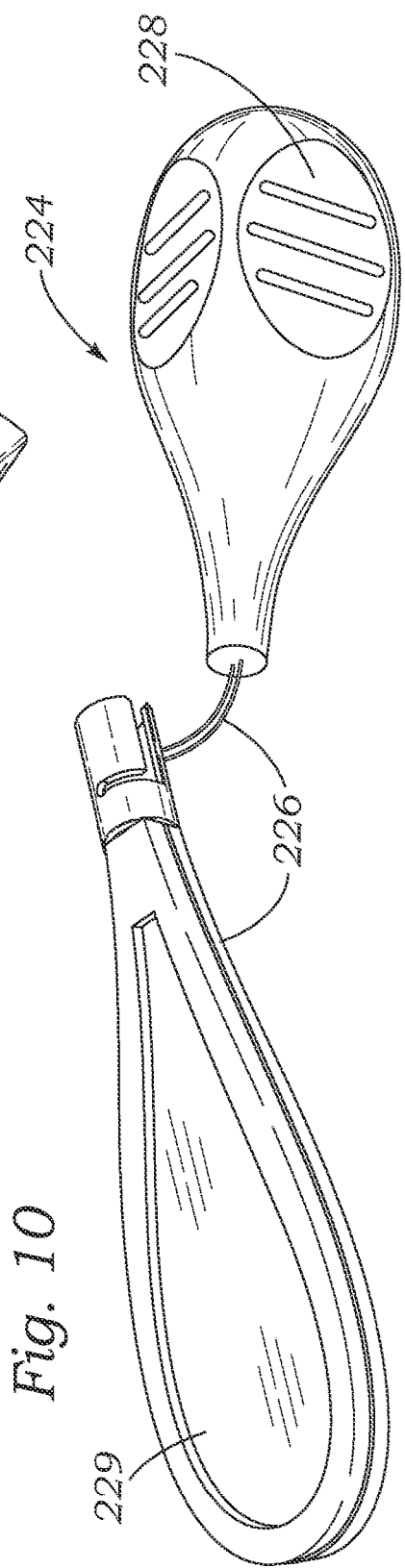

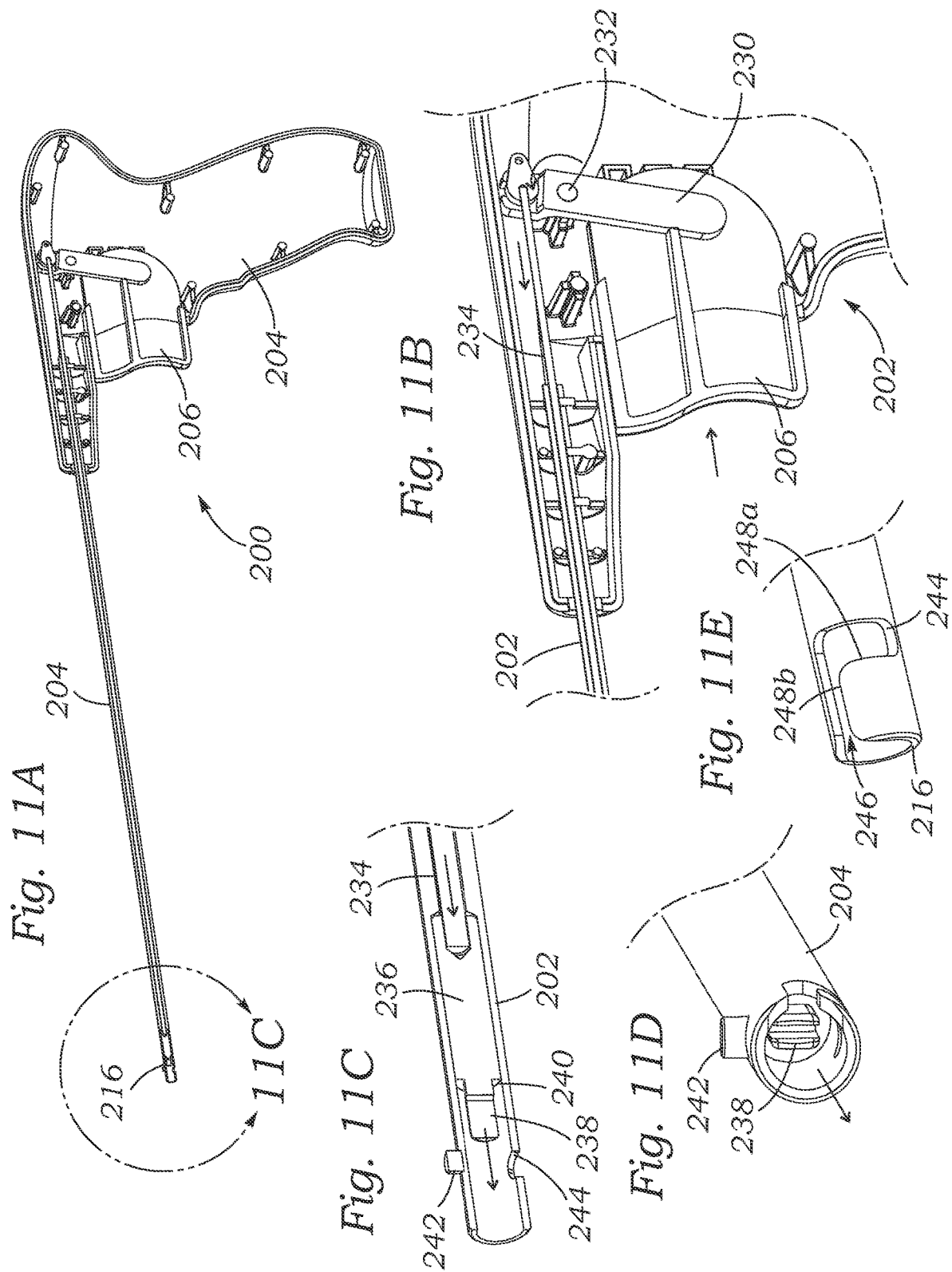

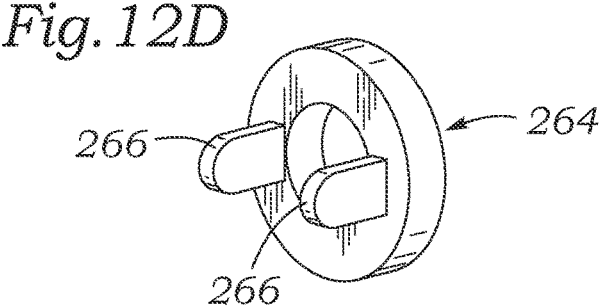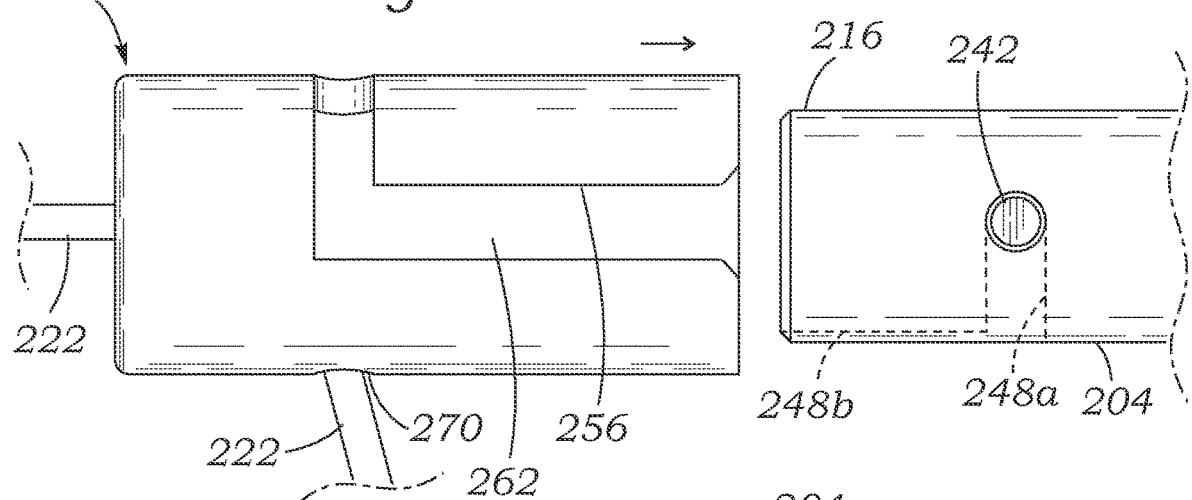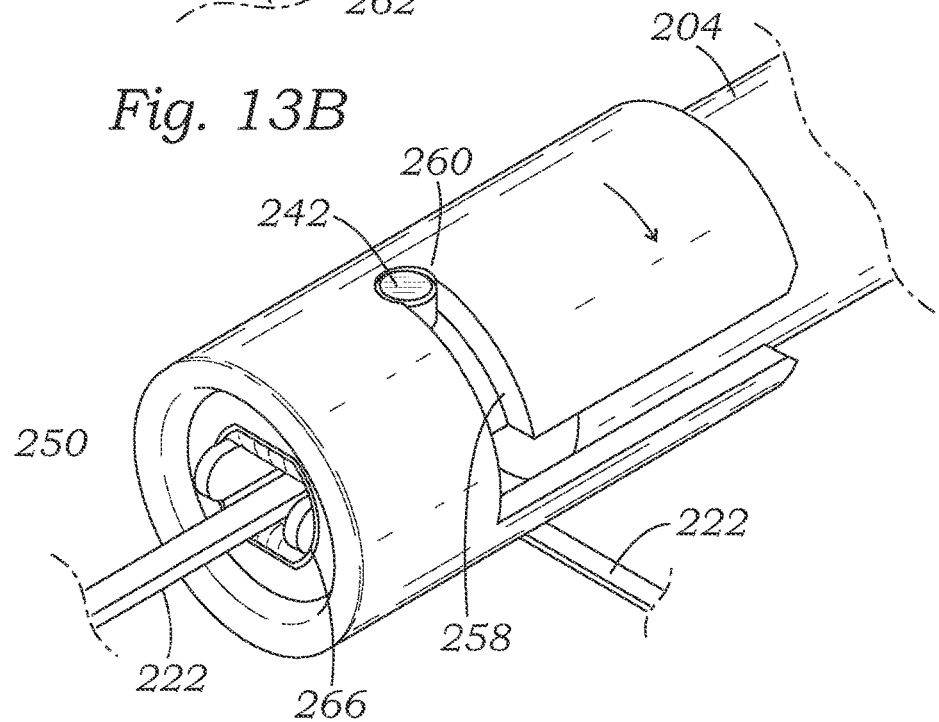

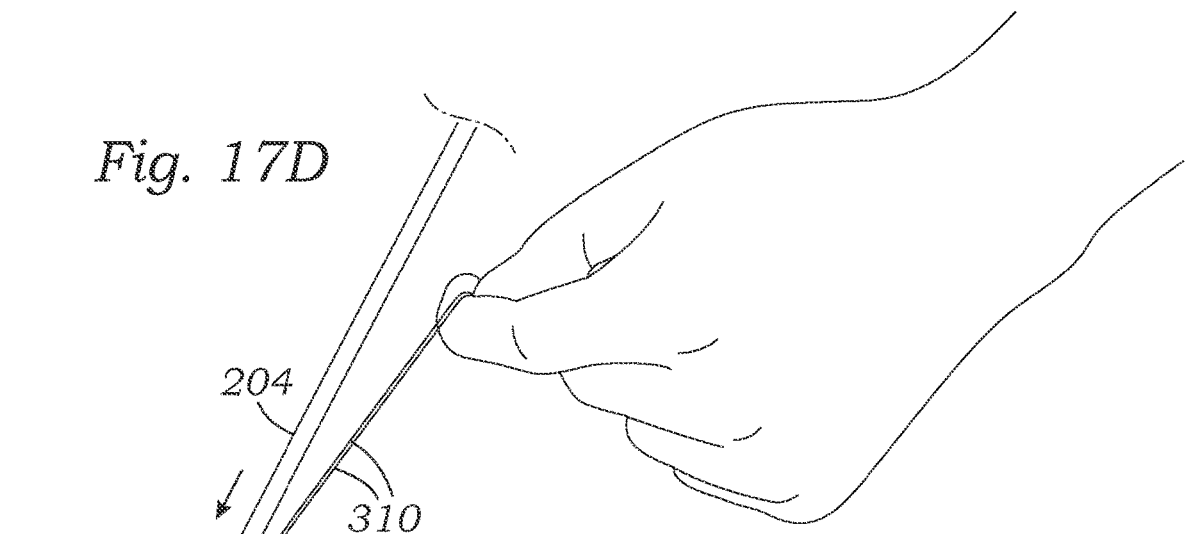
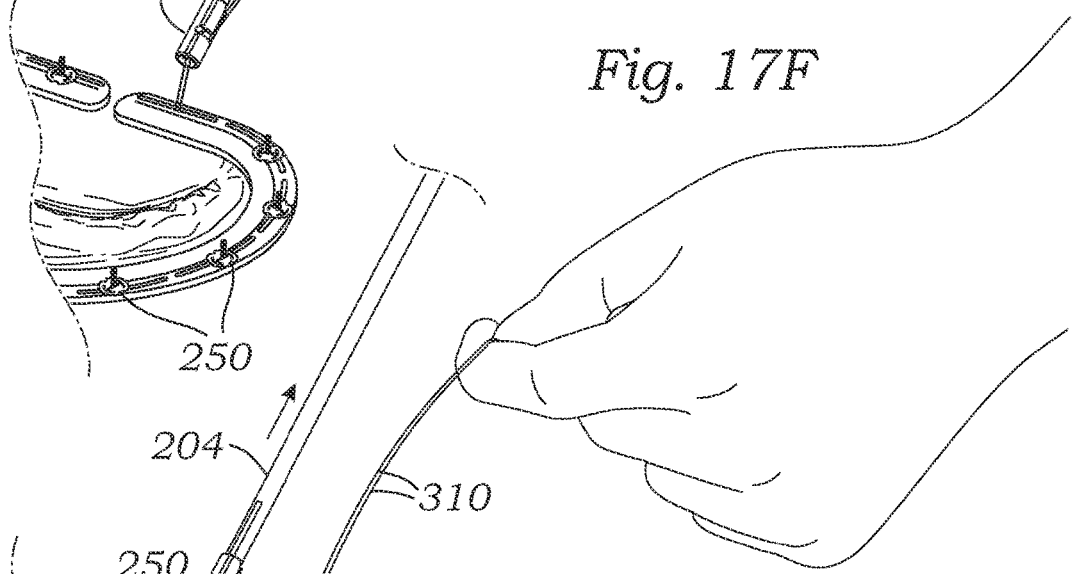
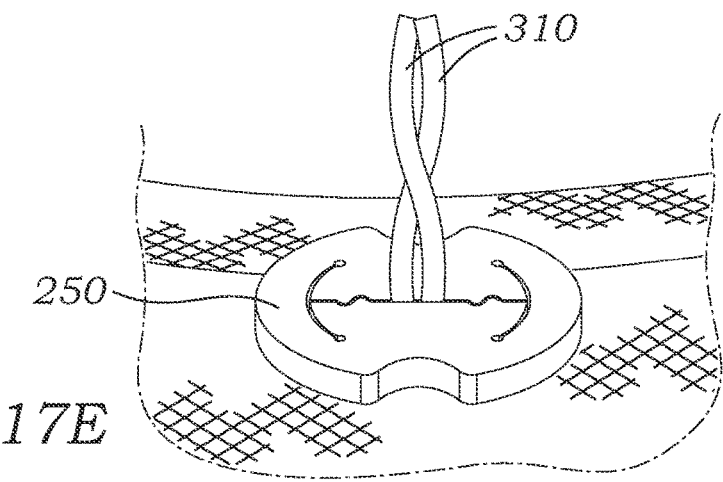
Fig. 17D
Fig. 17F
Fig. 17E

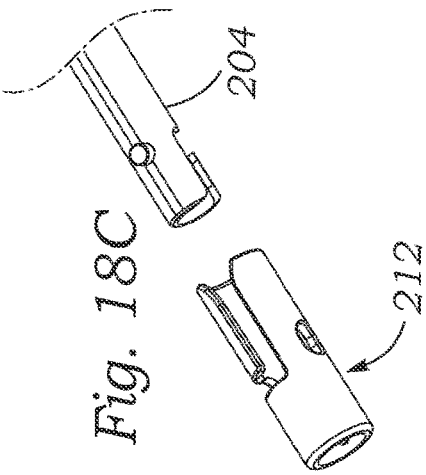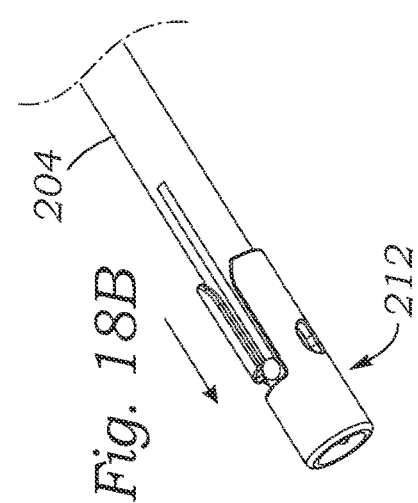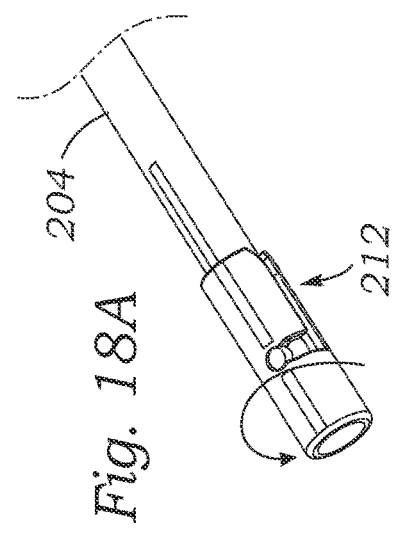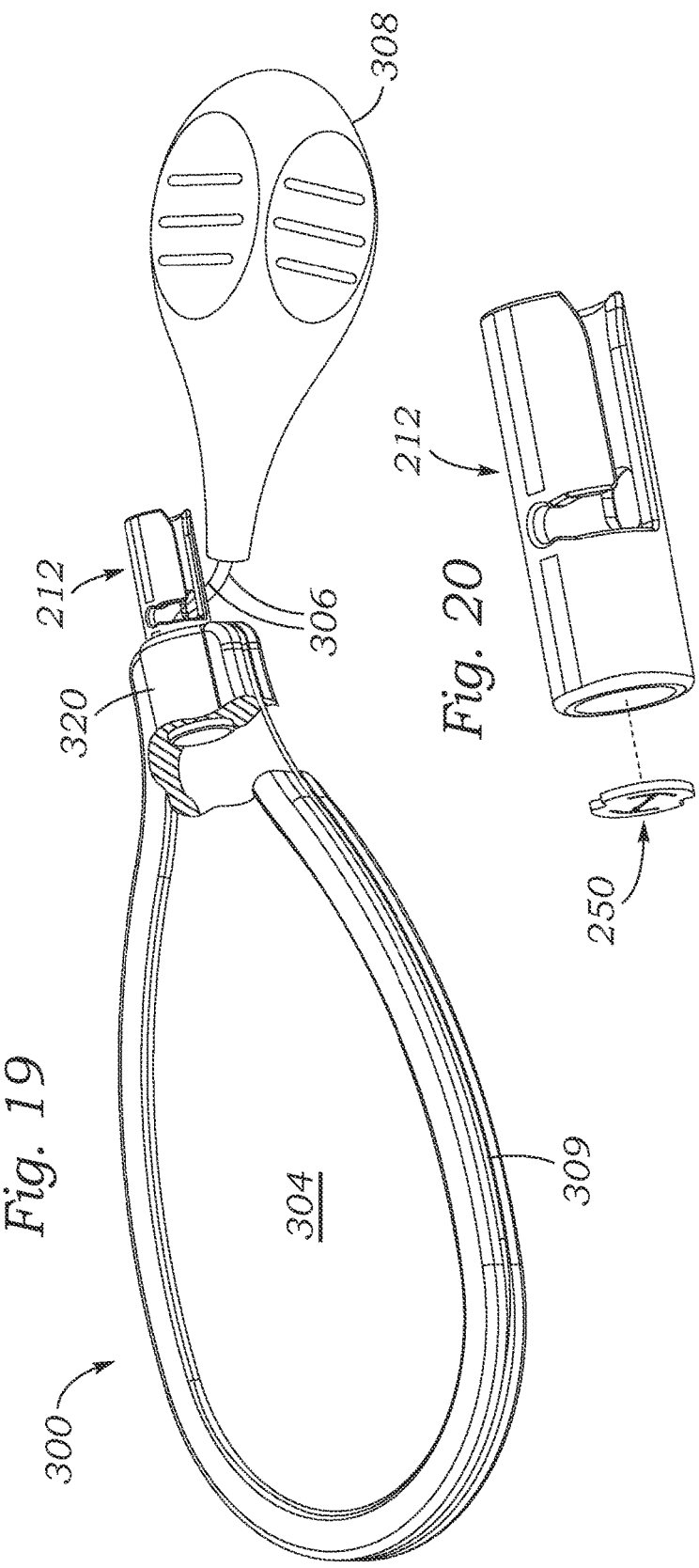

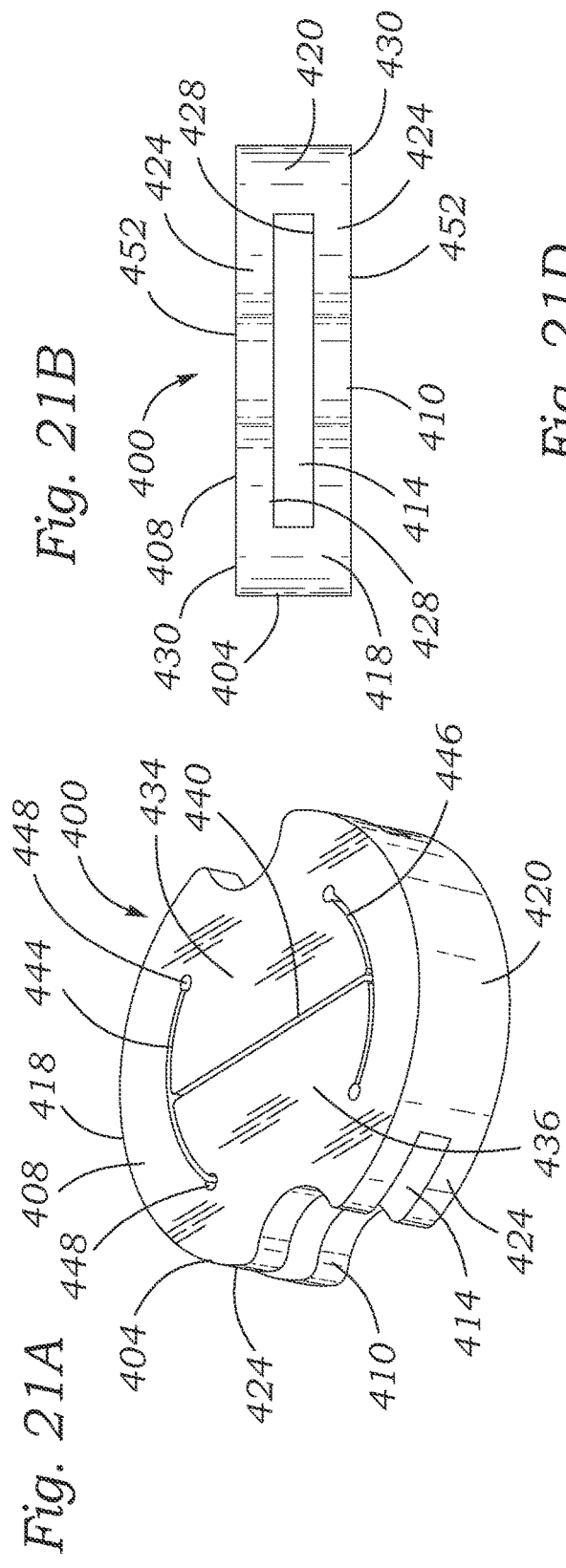
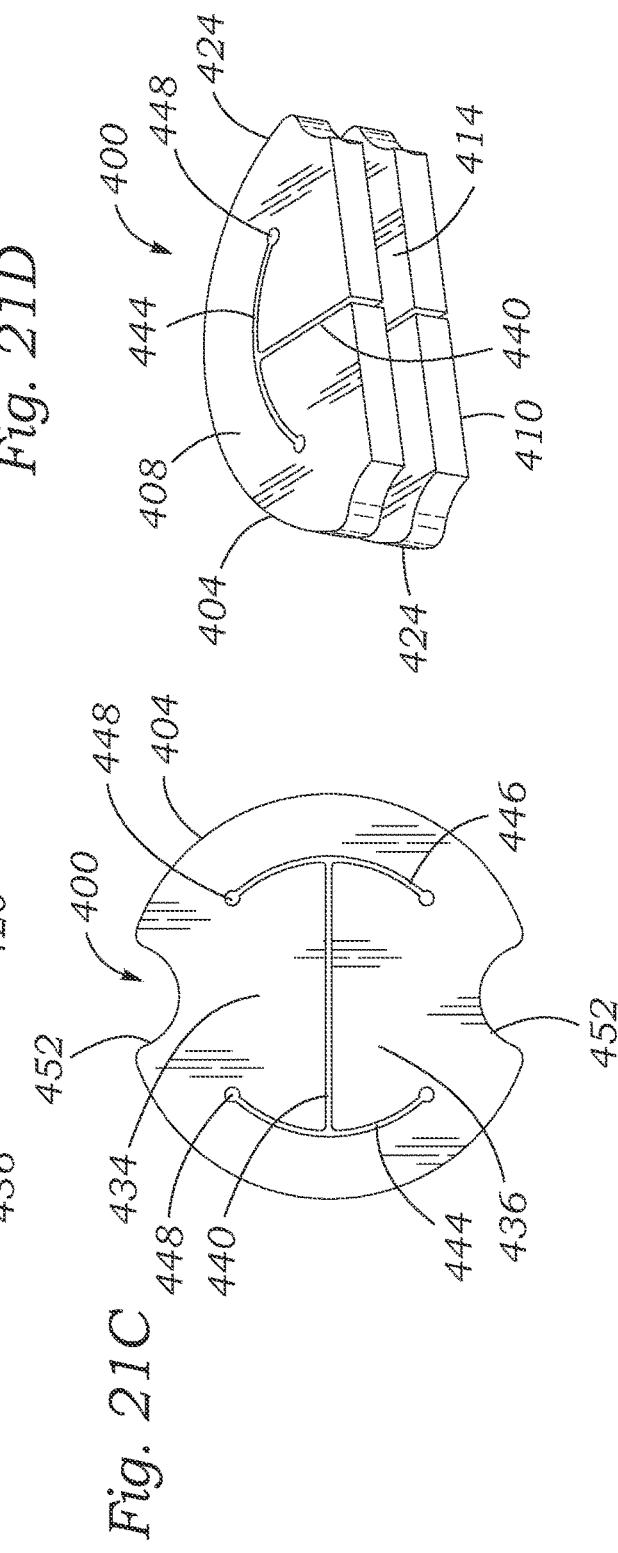

SUTURE FASTENER HAVING SPACED-APART LAYERS

CROSS REFERENCE TO RELATED APPLICATION

This application is a continuation of U.S. patent application Ser. No. 17/119,924, filed Dec. 11, 2020, which is a continuation of U.S. patent application Ser. No. 15/847,690, filed Dec. 19, 2017, now U.S. Pat. No. 10,863,980, which claims the benefit of U.S. Patent Application No. 62/439,868, filed Dec. 28, 2016, the entire disclosures all of are incorporated by reference for all purposes.

FIELD

This disclosure relates generally to suture fasteners, including systems and methods for their installation.

BACKGROUND

Heart valve disease is a widespread condition in which one or more of the valves of the heart fails to function properly. Various surgical techniques may be used to repair a diseased or damaged valve, including securing a cardiac implant to a diseased annulus. Cardiac implants can include prosthetic heart valves and annuloplasty rings.

In a typical valve replacement operation, damaged heart valve leaflets are excised and the annulus sculpted to receive a replacement valve. About one-half of patients receive a mechanical heart valve, which is often made from rigid, synthetic materials, and the remaining patients receive bioprosthetic heart valve replacements, which use biologically derived tissues for flexible, fluid occluding leaflets.

Another, less drastic, method for treating defective valves is through repair or reconstruction, which is typically used on minimally calcified valves. One repair technique that has been shown to be effective in treating incompetence is annuloplasty, in which the deformed valve annulus is reshaped by attaching a prosthetic annuloplasty repair segment or ring to the valve annulus.

In a typical cardiac implant procedure, the aorta is incised and, in a valve replacement operation, the defective valve is removed, leaving the desired placement site that may include a fibrous tissue layer or annular tissue. Known cardiac implant techniques include individually pre-installing sutures through the fibrous tissue or desired placement site within the valve annulus to form an array of sutures. Free ends of the sutures are draped out of the thoracic cavity and are spaced apart, sometimes being distributed around a suture organizer. The free ends of the sutures are then individually threaded through a suture-permeable sewing edge of the annuloplasty ring or prosthetic heart valve.

Once all sutures have been run through the sewing edge (typically 12 to 18 sutures), all the sutures are pulled up taught and the prosthesis is slid or "parachuted" down until it sits against the target annulus. The cardiac implant is then secured in place by traditional knot tying of the anchoring sutures on the proximal side of the sewing edge. There are often 7-10 knots on each suture advanced by pushing the knots one at a time to the desired location by using a knot pusher device. This procedure can be time-consuming.

During open-heart procedures, the patient is typically on heart-lung bypass, which can reduce the patient's oxygen level and create non-physiologic blood flow dynamics. The longer a patient is on heart-lung bypass, the greater the risk for complications, including permanent health damage.

Existing techniques for suturing cardiac implants can extend the duration of bypass and increase the health risks due to heart-lung bypass. Furthermore, the securing force created by suturing varies significantly because the pre-tensioning of the suture just prior to knot tying can be difficult to consistently maintain, even for an experienced medical professional. Additionally, a clinician must often work in the limited space near the heart to tie knots in sutures. This can be a cumbersome process even for a clinician of great dexterity and patience.

SUMMARY

Disclosed herein are embodiments of an improved suture fastener, and systems and methods for their use. The fasteners, systems, and methods can be used, for example, in securing heart valve repair or replacement prostheses in or near the heart. The devices and methods are particularly well suited for traditional or minimally invasive surgery. The fasteners can eliminate the need for surgical knots, thus reducing surgical time and exposure. Further, the fasteners can improve the ease of implantation, because the clinician need not tie knots in the limited space in and around the heart. Compared with other suture fasteners, the present disclosure can provide multi-layer suture fasteners than can provide for more secure suture retention, and the ability to sever suture more closely to the surface of the fastener, which can reduce the length of suture tails.

Some embodiments of a multi-layer suture fastener include a generally disc-shaped body defining a plurality of axially spaced-apart layers. Each layer can include an inner axial surface and an outer axial surface. A suture opening can extend from the inner axial surface to the outer axial surface of each layer. The suture openings can have an open configuration and a closed configuration. One or more lines of suture can be passed through the suture openings when in the open configuration. The suture openings can be placed in the closed configuration. In the closed configuration, the one or more lines of suture can be restricted by radial surfaces of the suture opening from sliding through the suture openings in at least one longitudinal direction of the one or more lines of suture.

In some implementations, the suture openings can be plastically deformable from the open configuration to the closed configuration. For example, the suture fastener can be crimped or compressed by a deployment tool. In further implementations, the suture opening can be elastically deformable. For example, the suture openings can be biased in the closed position. A deployment tool can elastically deform the suture fasteners such that the suture openings obtain the open configuration. One or more lines of suture can be inserted through the suture openings, and then the suture openings can resume the closed configuration, such as after being released from the deployment tool.

In further aspects, the suture openings can be radially, axially, or both radially and axially aligned. In other aspects, two or more of the axially spaced-apart layers can have suture openings that are not radially, axially, or both radially and axially aligned.

In particular implementations, the plurality of axially spaced-apart layers can include first and second tabs extending, respectively, from first and second sides of an annular outer surface of the layers. A pair of curved slots can pass through the layers inwardly from the annular outer surface of the layer defining the two tabs. The suture openings can include a middle slit that connects the curved slots and separates the tabs.

At least a portion of the area between each of the plurality of axially spaced-apart layers can be hollow, empty, or otherwise devoid of material. In some cases, at least a portion of the outer radial surfaces of the plurality of layers is axially contiguous about an outer radial surface of the device. In more specific examples, at least a portion of the outer radial surfaces of the plurality of layers are not axially contiguous about the outer radial surface of the device. For example, the non-contiguous portions can define apertures to the empty portion of the suture fastener between the axially spaced-apart layers.

In a further embodiment, the present disclosure provides a suture fastener deployment system. The system can include a deployment device that includes a handle, a shaft extending from the handle, a fastener deployment mechanism disposed at a proximal end of the shaft, and an actuator coupled to the handle and configured to active the deployment mechanism. The system can further include a suture fastener having a generally disc-shaped body defining a plurality of axially spaced-apart layers, such as a fastener described above. One or more lines of suture can be passed through suture openings formed in the axially spaced-apart layers when the suture openings are in an open configuration. The suture openings can obtain the closed configuration when the deployment mechanism is active by the actuator. When the suture openings are in the closed configuration, the one or more lines of suture are restricted from sliding through the suture openings in at least one longitudinal direction of the one or more lines of suture.

In some implementations, the deployment mechanism can plastically deform the suture fastener. In other implementations, the deployment mechanism can elastically deform the suture fastener such that the suture openings are held in the open configuration during deployment.

According to another embodiment, the present disclosure provides a method for securing one or more lines of suture. One or more lines of suture are installed at an anatomical location. The one or more lines of suture are passed through a suture fastener. The suture fastener include a generally disc-shaped body defining a plurality of axially-spaced apart layers. The layers each include an inner axial surface, an outer axial surface, and a suture opening extending from the inner axial surface to the outer axial surface. The suture openings have an open configuration and a closed configuration and are configured to receive the one or more lines of suture in the open configuration and secure the one or more lines of suture in the closed configuration. The suture fastener can be, for example, a suture fastener described above.

With a deployment tool, the suture openings can be manipulated from the open configuration to the closed configuration, thereby securing the one or more lines of suture against movement in at least one longitudinal direction of the one or more lines of suture. In some implementations, manipulating the suture openings from the open configuration to the closed configuration can include plastically deforming the suture fastener. In other implementations, manipulating the suture openings from the open configuration to the closed configuration can include elastically deforming the suture fastener during deployment, where the suture openings elastically resume the closed configuration after deployment of the suture fastener about the one or more lines of suture.

The foregoing and other objects, features, and advantages of the disclosed technology will become more apparent from the following detailed description, which proceeds with reference to the accompanying figures.

BRIEF DESCRIPTION OF THE DRAWINGS

FIG. 3A is a perspective view of an exemplary suture fastener having two tabs that are separated from a generally disc-shaped body by a modified H-shaped slit.

FIG. 3B is another perspective view of the suture fastener of FIG. 3A, showing the fastener engaged with two sutures.

FIG. 3C is a perspective view of another suture fastener again having two tabs and a suture retention recess on each.

FIG. 3D is a perspective view of another suture fastener with two tabs and serpentine sections on both sides of a central slit to help retain sutures therein.

FIGS. 7 and 8 are perspective views of two other suture fasteners having two tabs that are separated from a curved body.

FIG. 9 is a perspective view of an exemplary system for installing the suture fasteners disclosed in the present application, including a reusable deployment tool and a disposable fastener cartridge and snare subassembly.

FIG. 9A is an enlarged perspective view of the disposable fastener cartridge and snare subassembly adjacent the distal end of the deployment tool.

FIG. 10 is a perspective view of an alternative disposable fastener cartridge and snare subassembly.

FIG. 11A is a longitudinal sectional view of the deployment tool of FIG. 9.

FIGS. 11B-11E are sectional and perspective views of portions of the deployment tool illustrating various moving parts therein.

FIG. 12D is an isolated perspective view of an exemplary internal rib used within the fastener cartridge of FIG. 12A.

FIG. 13A is a top plan view of the disposable fastener cartridge just prior to engagement with a distal tip of the deployment tool, and FIG. 13B is a perspective view of the fastener cartridge after engaging the deployment tool, and showing placement of a suture snare therethrough.

FIGS. 17A-17F show sequential steps in operation of the deployment tool and fastener cartridge during installation of a suture fastener on the proximal side of an annuloplasty ring.

FIGS. 18A-18C show the steps of an example method for disengaging a used fastener cartridge from the distal tip of the deployment tool.

FIG. 19 is a perspective cutaway view of the exemplary disposable fastener cartridge of FIGS. 16A-16D.

FIG. 20 is an exploded perspective view of the fastener cartridge and a suture fastener that is held therein.

FIG. 21A is a perspective view of a suture fastener having multiple axially spaced-apart layers.

FIG. 21B is an elevational view of the suture fastener of FIG. 21A.

FIG. 21C is a plan view of the suture fastener of FIG. 21A.

FIG. 21D is a perspective, cross-sectional view of the suture fastener of FIG. 21A.

DETAILED DESCRIPTION

Figure 1:
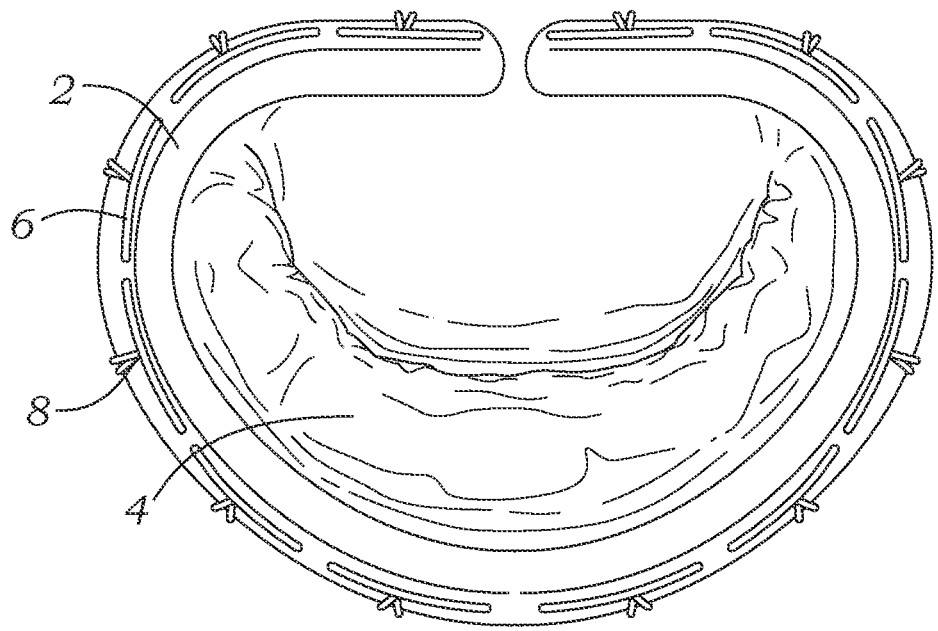
FIG. 1 is a top view of an exemplary annuloplasty ring implanted at the mitral annulus using knotted sutures.

The present disclosure provides fasteners, such as suture clips, and systems and methods for their deployment. In particular examples, the suture clips and deployment systems can be used for securing a cardiac implant to a heart valve annulus. "Proximal" and "distal" can refer to the opposite directions toward, and away from, respectively, a surgeon performing a procedure using the suture clips.

The term cardiac implant as used herein can refer to prosthetic heart valves and annuloplasty rings or segments. However, the suture fastening systems described herein can be used to attach other prostheses, such as stents, grafts, stent-grafts, fluid delivery reservoirs, electro-stimulators, artificial chordae, or the like. Furthermore, the cardiac implants are desirably secured at a target heart valve annulus, but the suture fastening systems may also be used to attach implants to other anatomical structures such as vessels, organs (e.g., intestine, heart, skin, liver, kidney, stomach) or other locations where sutures are typically used to attach the implant. Indeed, the present suture fastening systems can be used to secure tissue structures together, such as for approximating tissue, closing vascular punctures, or closing other wounds.

Several exemplary embodiments of suture fasteners are disclosed herein and shown in the accompanying figures. These embodiments should not be construed as limiting in anyway. Instead, the present disclosure is directed toward all novel and nonobvious features and aspects of the suture fastening systems described herein, alone and in various combinations and sub-combinations with one another, and regardless of what type of suture fastener is used. The suture fasteners can secure a single suture or to two or more sutures at the same time.

The disclosed suture fasteners can engage a suture by first threading a free end of the suture through an opening in the fastener. For example, in the embodiment shown in FIGS. 3A-3D and 4A-4D, an end of a suture can be threaded through an enclosed opening in the suture fastener. One or more biased tabs can be held open and then permitted to flex closed to clamp onto the suture. The tabs can be separated from a main body of the fastener by slits, and the main body can be generally disc-shaped, planar or non-planar. The various tabs and other such spring-biased structure are inclusively termed, "clamping structure."

While, in some cases, the suture fasteners can include biased tabs, in other cases, certain aspects described herein may be useful with closures (e.g., suture fasteners) that are plastically deformable. For example, the fasteners disclosed in U.S. Pat. No. 5,520,702 include a tubular body that is crimped so as to deform around and clamp onto a suture, and such deformable fastener may be used in the systems described herein with certain modifications, such as providing a deforming hammer.

Once a suture fastener is positioned on a suture and released, the fastener can prevent the suture from sliding axially through the device in one or both longitudinal directions of the suture. In some embodiments, the device can be biased to allow the suture to slide through the device in one longitudinal direction, but prevent the suture from sliding in the opposite direction, forming a one-way suture lock, or ratchet mechanism. In other embodiments, the device can prevent the suture from sliding in both longitudinal directions, forming a more restrictive two-way suture lock.

By using the disclosed suture fasteners rather than tying knots in the sutures, the sutures can be secured in less time and with less difficulty (especially in hard-to-reach locations). In addition, some suture fasteners can allow the amount of slack left in the sutures to be more precisely controlled, the devices can be less likely to come loose than knots, and some embodiments of the devices can be easily removed or adjusted after they are initially deployed. Furthermore, the suture fasteners can be small, durable, biocompatible, and inexpensive.

Figure 2:
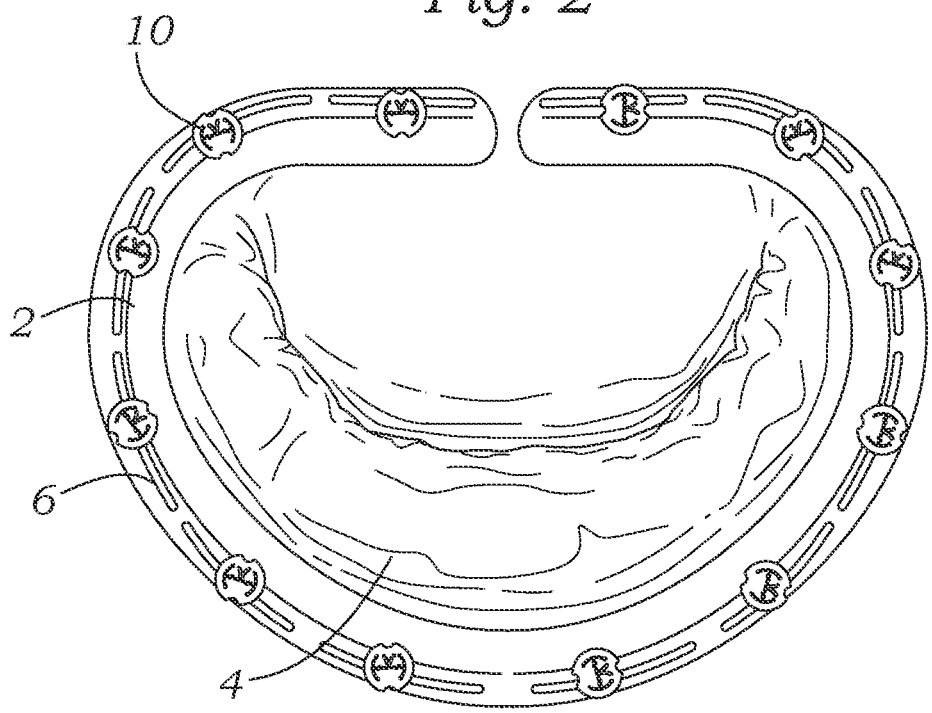
FIG. 2 is a top view of an exemplary annuloplasty ring implanted at the mitral annulus using exemplary suture fasteners in place of knots to secure the sutures.
Figure 4B:
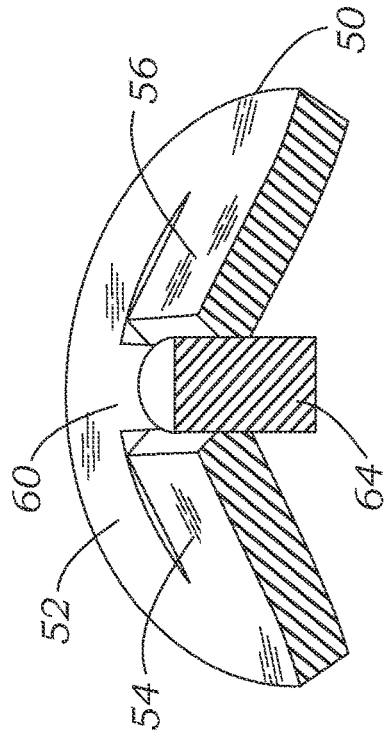
FIG. 4B is a sectional perspective view of the suture fastener of FIG. 4A engaged with a suture.
Figure 4D:
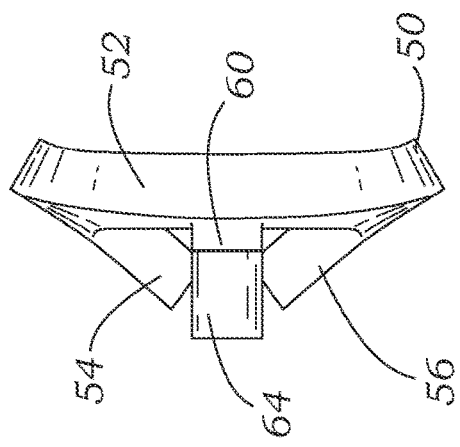
FIG. 4A is a perspective view of another exemplary suture fastener having four tabs that are formed in a generally disc-shaped body.
FIG. 4C is a plan view and FIG. 4D a side view of the suture fastener of FIG. 4A engaged with a suture.
Figure 4A:
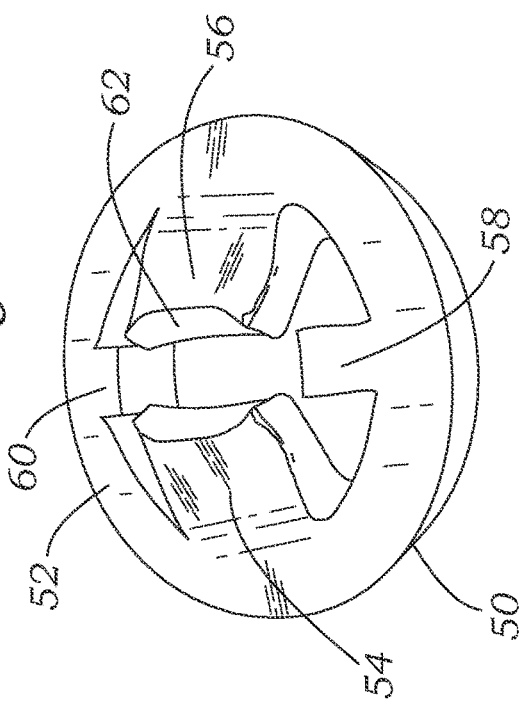
Figure 4C:
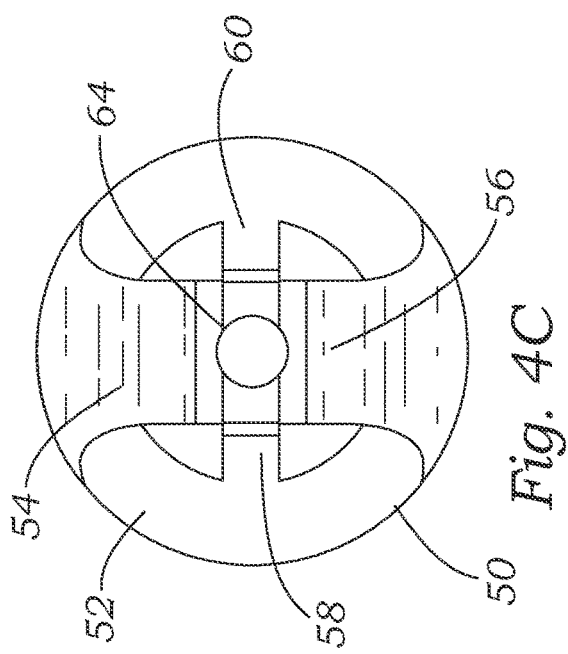

FIG. 1 shows an exemplary prosthetic device in the form of an annuloplasty ring 2 secured to the annulus of a native mitral valve 4 using sutures 6. Ends of the sutures 6 are secured together using conventional knots 8. FIG. 2 shows the same annuloplasty ring 2 secured to the mitral annulus using exemplary suture fasteners 10 instead of knots. Twelve devices 10 are used in this example, but different numbers of devices can be used in other implementations.

In this example, each device 10 secures together two sutures 6 extending generally in parallel and through the annuloplasty ring 2, in place of a standard knot. In other examples, a separate device 10 can be secured to each suture 6 at the location where the suture passes through the annuloplasty ring 2. Either way, the devices 10 can prevent the sutures 6 from sliding through the devices toward the annuloplasty ring 2, keeping the sutures taut, and keeping the ring 2 secured against the mitral valve tissue 4. In some embodiments, such as the devices 10 shown in FIG. 2, the devices also can allow the sutures 6 to be further tightened after an initial deployment to reduce any excess slack in the sutures. Though the exemplary suture fasteners 10 are shown in the example of FIG. 2, any of the embodiments disclosed herein can be used for the same or similar purposes on other implementations.

While FIG. 2 shows an annuloplasty ring being secured by devices 10, the devices 10, as well as the other embodiments of suture fasteners disclosed herein, can be used to secure other prosthetic devices to tissue in the body. Other prosthetic devices include, for example, prosthetic heart valves, stents, grafts, and various other prosthetic implants conventionally secured to tissue using sutures.

FIGS. 3A and 3B show embodiments of a closed, non-biased suture fastener 30. The suture fastener 30 can comprise a generally flat disc-shaped body having an annular outer edge 32 and two tabs 34, 36, which can act as a clamping structure, that extend inwardly from the outer edge 32. Each tab 34, 36 can be shaped generally in a half-circle. The tabs 34, 36 can be separated from the outer body at their sides by curved slots 38, 40, and can be separated from each other by a straight slit 42 generally bifurcating the suture fastener 30. The curved slots 38, 40 and middle slit 42 can connect to each other, but do not intersect with an outer edge 32, in the illustrated embodiment. Thus, the curved slots 38, 40 and the middle slit 42 can form a "closed," generally H-shaped opening extending from one face of the suture fastener to the other.

In the closed condition, the tabs 34, 36 can be aligned with the disc-shaped body. One or more sutures 43 can be inserted into the slit 42 from either the top or the bottom, deflecting both tabs 34, 36 in the direction of insertion, as shown in FIG. 3B. Once the sutures 43 are inserted as shown in FIG. 3B, the suture fastener 30 can be biased toward its relaxed, flat configuration, and allow the sutures to move axially upward with little resistance, but prevent the sutures from moving axially downward. In some embodiments, at least a portion of the gripping edges of the tabs 34, 36 can be sharp (see FIG. 3A), which can provide a better grip on the sutures. In other embodiments, at least a portion of the gripping edges of the tabs 34, 36 are not sharp, for example, can be rounded (see FIG. 3B), which can reduce the likelihood of damaging and/or cutting the sutures.

In some implementations of the suture fastener 30 (not shown), the two tabs 34, 36 can be elastically deformed in opposite directions, with one tab bending upwardly out-of-plane and the other tab bending downwardly out-of-plane. This can lock the sutures from sliding in either direction through the suture fastener 30. The two sutures 43 shown in FIG. 3B can correspond to free ends of the sutures 6 shown in FIG. 2, for example.

FIG. 3C shows a suture fastener 44 that is a variation of the suture fastener 30, wherein the gripping surfaces of the tabs 34, 36 comprise notched or recess regions 45 that can help contain the sutures within the slit 42 and prevent them from sliding into the curved slits 38, 40.

FIG. 3D shows a further variation, a suture fastener 46 having a flat generally disc-shaped body having an annular outer edge 32' and two tabs 34', 36', which can act as a clamping structure, that extend inwardly therefrom. As in FIG. 3A, each tab 34', 36' can be shaped generally in a half-circle. The tabs 34', 36' can be separated from the outer body at their sides by curved slots 38', 40', and can be separated from each other by a slit 42' that has a straight midsection. Once again, the curved slots 38', 40' and middle slit 42' can connect to each other, but not intersect with an outer edge of the body 32', thus forming a "closed," generally H-shaped opening extending from one face of the suture fastener to the other. In a closed configuration, the tabs 34', 36' can be aligned with the disc-shaped body.

One or more sutures can be inserted into the slit 42 from either the top or the bottom, deflecting both tabs 34, 36 in the direction of insertion, as was shown in FIG. 3B. Once the sutures 43 have been inserted in the slit 42, the suture fastener 46 can become biased, allowing the sutures to move axially upward with little resistance, but preventing the sutures from moving axially downward. As mentioned above, the gripping edges of the tabs 34, 36 may be sharp for better grip on the sutures, or rounded to reduce the likelihood of damaging and/or cutting the sutures.

To help retain sutures in the midsection of the slit 42', the slit can include serpentine sections 47 on either side. The tabs 34', 36' can be identical, or mirror images of each other, though one may be larger than the other. Small circular enlargements 48 on the terminal end of each curved slot 38', 40' can facilitate bending of the tabs 34', 36', and can act as stress relievers to reduce the chance of fracture at those points. Two semi-circular cutouts 49 can be provided on opposite sides of the outer edge 32', perpendicular to the straight section of the slit 42'. The cutouts 48 can provide an orientation feature for the suture fastener 46 that can cooperate with features on a tool (not shown), which can hold and deploy multiple suture fasteners in series.

FIGS. 4A-4D show an embodiment of a closed, biased suture fastener 50. The suture fastener 50 can comprise an annular outer body 52, two engagement tabs 54, 56, and two side tabs 58, 60 extending inwardly from the outer body 52. The tabs 54, 56 and/or the tabs 58, 60 can also extend upwardly out-of-plane from the outer body 52. The engagement tabs 54, 56 can comprise concave engagement surfaces 62 to keep the suture 64 centered between therebetween. The side tabs 58, 60 can reduce or prevent the suture 64 from sliding laterally out from between the engagement tabs 54, 56. The engagement tabs 54, 56 can be biased to allow the suture 64 to slide upwardly through the suture fastener 50 with little resistance but prevent the suture from sliding downwardly through the suture fastener.

Some suture fasteners can be relatively thin, disc-shaped members, but have a generally curved rather than a planar shape. The embodiments shown in FIGS. 5-8 are examples of suture fasteners having a curved shape. In these embodiments, the suture fastener can have an upper or first major surface that is generally convex and a lower or second major surface that is generally concave. The upper and lower major surfaces can be substantially parallel to each other, with the suture fasteners having a substantially constant thickness between the two major surfaces.

In some embodiments, the upper and lower major surfaces can be curved in one direction and non-curved in a perpendicular direction (like a sidewall of a cylinder), such that the surfaces have central axis of curvature. In some embodiments, both major surfaces can have a common central axis of curvature. In other embodiments, the major surfaces can be curved in other manners, such as having concentric spherical major surfaces that share a common center of curvature. By providing suture fasteners with a curved structure, the fasteners can be biased to provide greater resistance to sutures moving toward the concave direction while more readily allowing sutures to move toward the convex direction.

In some embodiments, such curved suture fasteners can be formed from a sidewall of a tube. The outer radius of the tube can define the curvature of the convex major surface of the suture fastener while the inner radius of the tube can define the curvature of the concave major surface of the device. The uniform thickness of a curved suture fastener can be equal to the wall thickness of the tube that the device is cut from. In other embodiments, the suture fasteners can be formed from a sidewall of a non-cylindrical tube, or from a wall of other three-dimensional objects having a curved wall, such as a hollow sphere, spheroid, ellipsoid, etc., or from other three-dimensional objects having a curvature, for example, a saddle shape.

Figure 5:
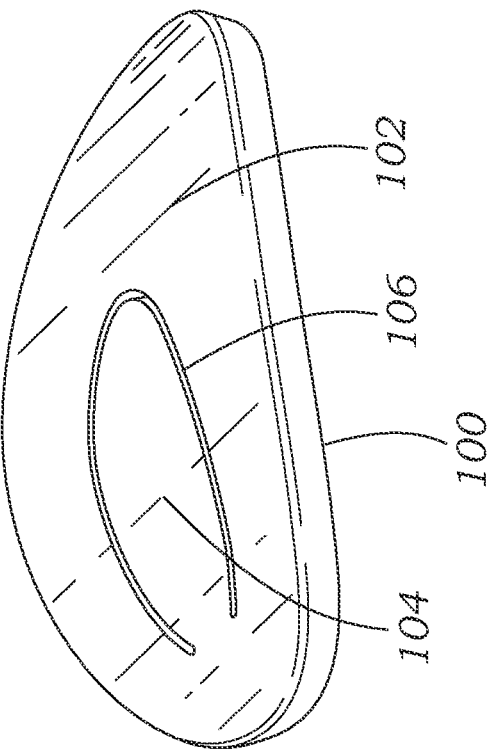

FIG. 5 shows an exemplary embodiment of a curved suture fastener 100. The suture fastener 100 can comprise an annular outer body 102 and an inner body, or tab, 104 that can be separated from the outer body by a "C" shaped slit 106. The convex, upper major surface of the suture fastener 100 is shown in FIG. 5. The tab 104 can have an elliptical shape and extend from a connection to the outer body in the direction of the curvature of the suture fastener. One or more sutures can be inserted through the slit 106 from the concave, lower side of the suture fastener 100, causing the tab 104 to deflect upwardly. With sutures inserted through the slit 106, the biased tab 104 can pinch the sutures, and prevent them from sliding back through the slit toward the concave direction. Thus, the suture fastener 100 can be attached to sutures with the concave side of the fastener facing a prosthetic device or tissue from which the free ends of the sutures extend.

Figure 6:
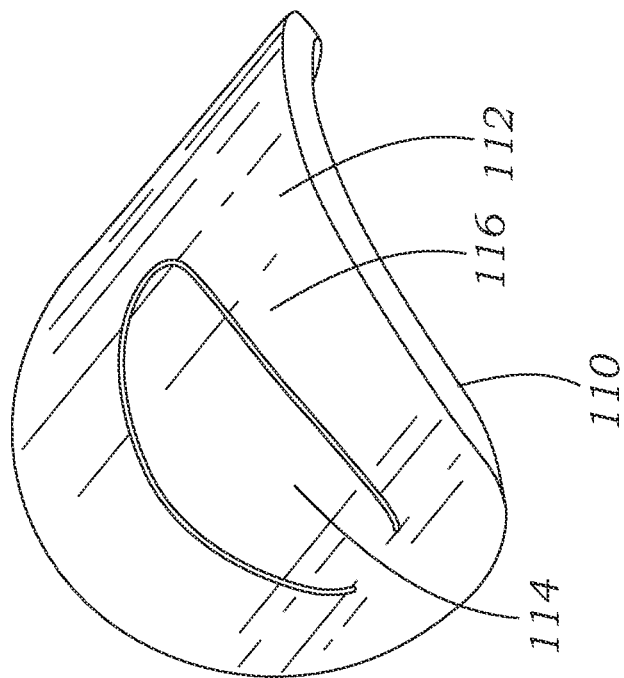
FIGS. 5 and 6 are perspective views of exemplary curved suture fasteners having C-shaped slits forming a biased tab.

FIG. 6 shows an alternative embodiment of a curved suture fastener 110 that can be similar to the fastener 100, but have greater curvature. The suture fastener 110 can comprise an annular outer body 112, an inner tab 114, and a "C" shaped slit 116. The increased curvature of the suture fastener 110 relative to the fastener 100 can result in increased bias, and increased resistance to sutures sliding through the slit 116 toward the concave direction. The embodiments 100 and 110 represent two examples of different curvatures, while other embodiments can have any other degree of curvature desired. Similarly, the thickness of the curved suture fasteners may vary, and is typically selected to provide a desired stiffness for the fastener.

FIG. 7 shows an embodiment of a curved suture securement suture fastener 120 that can comprise an annular outer body 122 and two opposing tabs 124, 126, which can be similar to a flat version shown in FIGS. 3A-3C. The outer body 122 can have a generally circular shape, and each of the tabs 124, 126 can have a generally half-circle shape. The tabs 124, 126 can be separated from the outer body by two arcuate slots 128, and the tabs can be separated from each other by a straight slit 129 that connects the two arcuate slots 128. One or more sutures can be inserted into the slit 129 from the lower convex side, deflecting both tabs 124, 126 upwardly in the direction of insertion. With the sutures inserted, the biased tabs can allow the sutures to move upwardly in the convex direction with little resistance, but prevent the sutures from moving downwardly in the concave direction.

FIG. 8 shows another embodiment of a curved suture securement suture fastener 130 that can comprise an annular outer body 132 and two opposing tabs 134, 136. The outer body 132 can have a generally circular shape, and each of the tabs 134, 126 can extend inwardly from opposite ends of the outer body. The tabs 134, 136 can be separated from the outer body by two arcuate slots 138, and the tabs separated from each other by a slit 139 that connects the two arcuate slots 138. The slit 139 can have a straight middle portion for placement of sutures and angled or L-shaped end portions 131 at either end of the straight portion that can help retain the sutures in the straight portion of the slit 139, and prevent the sutures from migrating into the arcuate slots 138. The two tabs 134, 136 are thus dissimilar, with the larger left tab 134 extending around the right tab 136 on both sides at the L-shaped end portions 131 of the slit 139. One or more sutures can be inserted into the slit 139 from the lower convex side, deflecting both tabs 134, 136 upwardly in the direction of insertion. With the sutures inserted, the biased tabs can allow the sutures to move upwardly in the convex direction with little resistance but prevent the sutures from moving downwardly in the concave direction.

The suture fasteners disclosed herein may be formed from suitable biocompatible materials, including, for example, nickel-titanium alloys (e.g., nitinol) or other shape-memory alloys, stainless steel, titanium, other metals, various plastics, and other biologically-compatible materials. The illustrated suture fasteners can have mostly flat, or curved, disc-shaped bodies which can be relatively thin axially, and, in some examples, may be up to about 1-2 mm in height. The diameter of the suture fasteners may be, in particular examples, between about 2-4 mm. In more specific examples, the suture fasteners can be sufficiently large to be incapable of penetrating a suture-permeable sewing edge of a cardiac implant, such as a sewing ring of a prosthetic heart valve or an annuloplasty ring. That is, the suture fasteners can be wide enough to avoid being pulled through a sewing edge of a cardiac implant when the sutures captured therein are placed under tension. In other examples, the fasteners may have a different height or diameter.

Braided sutures are typically used to attach prosthetic heart valves to annuluses, as opposed to monofilament polypropylene sutures (e.g., Prolene suture, Ethicon), which are often used in other surgical environments. In the United States, suture diameter can be represented on a scale descending from 10 to 1, and then descending again from 1-0 to 12-0. A number 9 suture is 0.0012 in (about 0.03 mm) in diameter, while the smallest, number 12-0, has a diameter of about 0.001-0.004 mm, which is thinner than a human hair. Although suture size can depend on surgeon preference, typically 1-0 or 2-0 braided sutures are used to attach prosthetic heart valves to annuluses. In one embodiment, if larger sutures are used, the diameter of the suture fastener can be up to about 4 mm, while if smaller sutures, such as 2-0, are used the diameter may be as small as about 2 mm.

The suture fasteners described herein can include self-actuating or spring-loaded devices that clamp onto sutures. Passing one or more sutures through the suture fastener, and then converting it from an open to a closed state, can cause features to collapse inwardly and clamp onto the suture(s). The conversion can desirably occur upon removal of an impediment to inward motion of clamping elements, though other spring-loaded configurations are possible. For added security, a supplemental portion (not shown) of the suture fasteners disclosed herein may be deformable so that a user may crimp it onto the sutures—a hybrid fastener.

For the purpose of defining terms, the term "self-actuating" suture fastener can refer to a spring-biased type of device which does not require crimping, but which, on the other hand, does not exclude a crimpable portion. A "self-actuating" suture fastener may not be entirely autonomous, in that there can be a trigger prior to the deployment, such as removal of an element or change in temperature, but the term excludes devices where all suture-retaining features require mechanical crimping using a supplemental tool, such as a hammer and anvil system.

Alternative self-actuating fasteners may be made of a temperature-activated memory material that biases the fastener to its closed configuration when exposed to a selected temperature range. With the temperature-activated memory material in its austenite state, the fastener tabs can extend into the inner lumen to their greatest extent, so that the fastener is in a "closed" configuration wherein the tabs block movement of any lengths of suture passing through the inner lumen. The austenite state can be set to occur when the suture fastener is generally unstressed and at human body temperature, so that when deployed in the patient's body it will be remain biased toward its closed configuration.

Fastener Deployment Tools

FIG. 9 shows an exemplary fastener deployment tool 200 that can be used to install the suture fasteners disclosed in the present application. The tool can have a proximal handle 202 and an elongated distal shaft 204 extending therefrom. The handle 202 can incorporate a trigger actuator 206, though other actuators are contemplated. The total length of the deployment tool 200, and at least the length of the shaft 204, should typically be sufficient to extend from outside the surgical site to the aortic annulus, such as between about 25-40 cm (about 10-16 inches), when used in a procedure involving a sewing ring of a prosthetic heart valve or an annuloplasty ring. In other examples, the deployment tool 200 can have a different length.

The deployment tool 200 can be intended to be reused during a surgical procedure, and can be made of materials that enable sterilization for a subsequent procedure. For instance, the outer shaft 204 can be made from stainless steel tube, and may be available in multiple lengths to facilitate a variety of surgical techniques, such as during heart valve repair or replacement, or for implant of other medical devices. An exemplary OD of the shaft 204 is about 3.2 mm (about ⅛ inch).

A subassembly 210 including a disposable fastener cartridge 212 and suture snare 214 can be configured to mate with a distal tip 216 of the deployment tool shaft 204, and as such is shown slightly removed therefrom in FIGS. 9 and 9A. The suture snare 214 may take a number of forms, and, as illustrated, includes a proximal pull tab 218 connected to a snare portion comprising a distal loop, hook or snare end 220 and a flexible wire or strip 222. The strip 222 can be flexible stainless steel, and may also be configured as a wire or wire loop as seen below. As will be explained below, the snare end 220 and flexible strip 222 can be fed through apertures and passages in the disposable fastener cartridge 212 so that the snare end extends from a distal end of, and generally along a central axis of, the cartridge as shown.

An alternative embodiment of a suture snare 224 shown in FIG. 10 can include a distal wire loop 226 connected to a proximal handle 228 in the form of a bulb. The wire loop 226 can be initially routed around a peripheral groove in a placement grip/key 229 for shipping, storage, and handling purposes, and to prevent kinking of the loop. Either of the suture snares 214, 224 may be used, and can provide a means for grasping one or more sutures and pulling them through passageways in the fastener cartridge 212. The length of the flexible strip 222 or wire loop 226 beyond the respective handle pull tab 218 or handle 228 can be sufficient to pass through the fastener cartridge 212 and extend beyond a sufficient distance to enable grasping of sutures; the length being, for example, between about 2-8 inches.

FIG. 11A is a longitudinal sectional view of the deployment tool 200 of FIG. 9 showing internal components, while FIGS. 11B-11D are detailed views illustrating key moving parts therein. More particularly, the handle 202 can comprise a pair of molded halves defining a cavity therein in which the trigger actuator 206 reciprocates. Pushing the actuator 206 inward, as indicated in FIG. 11B, can rotate a lever arm 230 about a pivot point 232. The upper end of the lever arm 230 can act via a linkage on a push rod 234 adapted to reciprocate within the hollow tool shaft 204. Consequently, the depression of the trigger actuator 206 can cause distal displacement of the push rod 234, while a spring return (not shown) of the trigger actuator can retract the push rod proximally.

With reference to FIGS. 11C and 11D, the distal end of the push rod 234 can fasten to a proximal end of a fastener ejector 236 having a main body portion which can fit closely in the lumen of the tool shaft 204. The ejector 236 can also have a pair of bifurcated fingers 238 projecting from a distal end. It should be noted that a distal shoulder 240 located at the transition between the main body of the ejector 206 and the distal fingers 238 can have a relatively sharp corner angle, the purpose of which will be described below.

As seen in FIGS. 11D and 11E, the distal tip 216 of the tool shaft 204 can also feature an outwardly projecting locking pin 242 and a side port 244 generally opposite the pin for cooperating with the fastener cartridge and suture snare subassembly 210. The side port 244 can open to the distal tip 216 via an L-shaped slot 246 having a circumferential portion 248a and an axial portion 248b. As will be described below with reference to coupling of the fastener cartridge 212 with the tool shaft 204, the L-shaped slot 246 can enable pull-through of the suture snare 214 upon registration of the shaft with the cartridge.

Figure 12A:
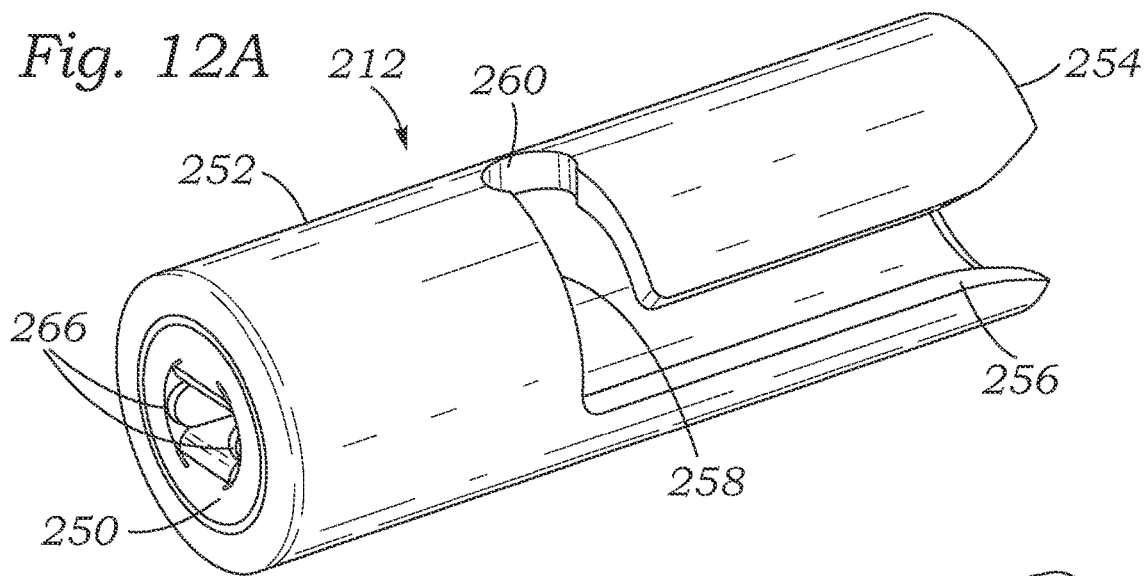
FIG. 12A is a perspective view of the distal end of an exemplary disposable fastener cartridge.

FIG. 12A is a perspective view of an exemplary disposable fastener cartridge 212, showing an exemplary suture fastener 250 held at a distal end thereof. The cartridge 212 can have a generally tubular body 252 with an open proximal mouth 254 with an axial slot 256 opening on one side thereof. The slot 256 can have a flared open end and intersect with a circumferential slot 258 approximately midway along the length of the cartridge body 252. The slot 258 can terminate at a circular lockout 260. The combination of the axial slot 256, circumferential slot 258, and lockout 260 can form a bayonet-style latch that can engage the distal tip 216 of the tool shaft 204, as will be shown.

It should be noted that the illustrated locking structure provided on the deployment tool shaft 204 that engages the mating structure on the cartridge 212 is exemplary only, and other such configurations are contemplated. For example, the cartridge 212 may include threads that engage similar threads on the tool shaft 204, or the connection may be a spring-loaded bearing on the shaft 204 which snap fits into a groove on the cartridge 212.

Figure 12B:
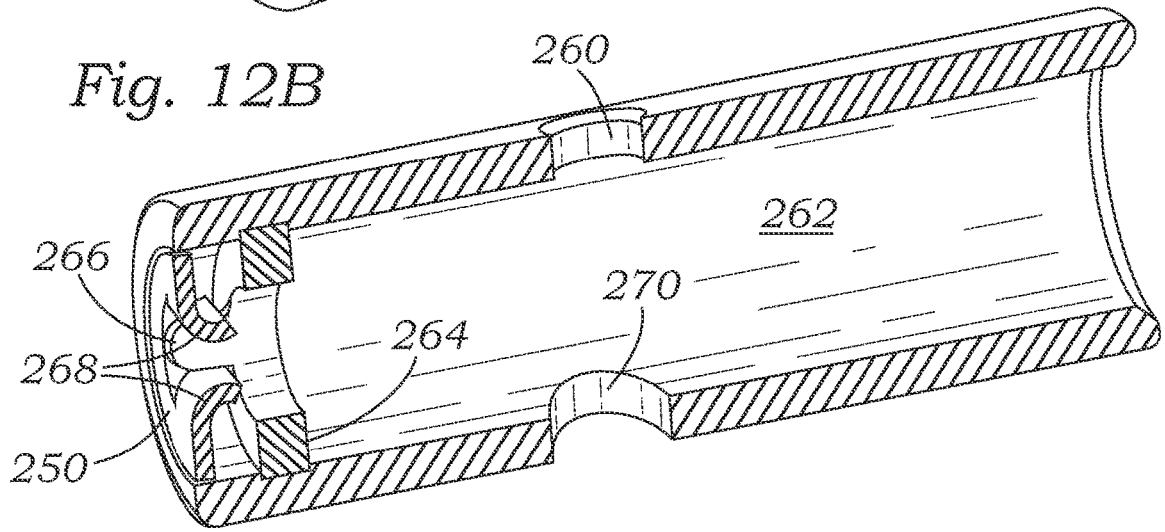
FIGS. 12B and 12C are sectional views of the fastener cartridge of FIG. 12A showing a fastener at the distal end held open by internal features, and illustrating the path of a suture snare therethrough.
Figure 12C:
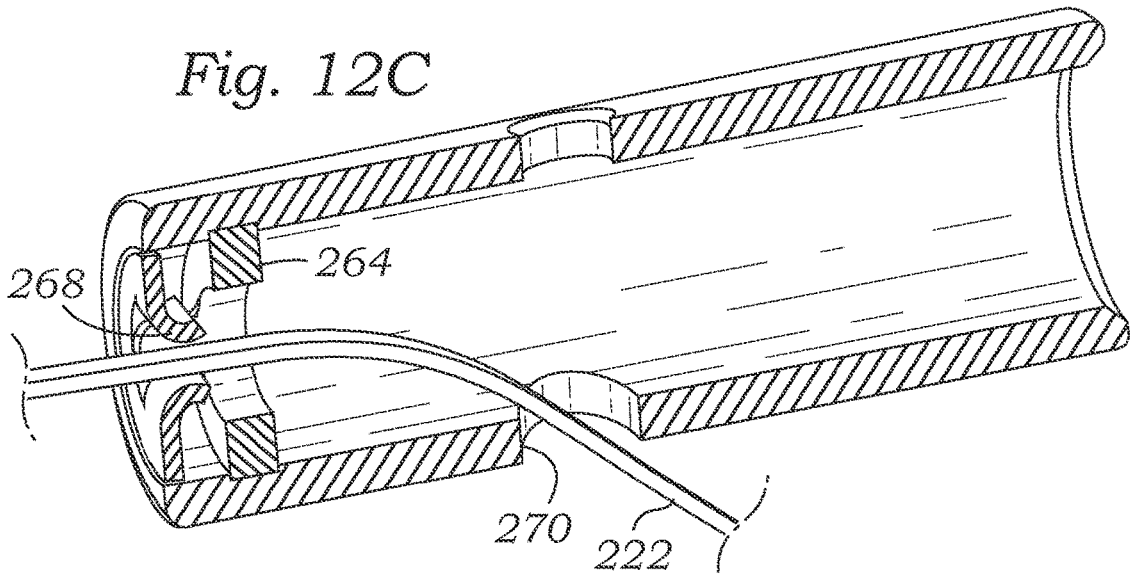

With reference to the sectional views of FIGS. 12B and 12C, the body 252 can define an inner lumen 262 that has a continuous diameter for most of its length except for a generally annular inwardly directed rib 264 near its distal end. The rib 264 can extend around the perimeter of the lumen 262 and have a pair of stops 266 projecting in a distal direction on opposite sides and spaced inward from the lumen 262. The stops 266 can hold open two biased tabs 268 on the suture fastener 250 for passage of the suture snare and, ultimately, the sutures. The rib 264 having the stops 266 is shown isolated in FIG. 12D, and can generally comprise a ring-shaped element with a square cross-section.

The disposable fastener cartridge 212 can comprise a thermoplastic molded over the rib 264, which is can be a metal, such as stainless steel or a cobalt-chromium alloy. The stainless steel rib 264 and its stops 266 can be sufficiently hard to maintain the suture fastener 250 in an open position without deformation, while the cartridge 212 as a whole can be a relatively inexpensive item. In any one procedure, ten or more of the cartridges 212 and fasteners 250 may be used and discarded with minimal expense. The deployment tool 200, in some cases, can be reused, at least for the one procedure, and then may be sterilized for subsequent use.

The fastener 250 may be any of the fasteners described above, such as those shown in FIGS. 3A-3D which have at least one and preferably two biased tabs 34, 36 separated from a generally disc shaped body by slits. Although not shown, those of skill in the art will understand that a separate assembly fixture (not shown) may be required to bias the tabs 268 open and load the fastener 250 into the position held open by the projections 266 as shown in FIGS. 12A-12C. The fasteners 250 are typically formed a highly flexible stainless steel or superelastic such as Nitinol.

The cartridge body 252 can also include an access port 270, typically located opposite the lockout 260. As seen in FIG. 12C, the flexible strip 222 of the suture snare 214 can pass into the access port 270, through the distal tip 216 of the tool shaft 204 (not shown), and distally through a central opening in the annular rib 264 and between the open suture fastener tabs 268. A full explanation of the cooperation between the various deployment components is provided below.

FIG. 13A is a top plan view of the disposable fastener cartridge 212 just prior to engagement with the distal tip 216 of the deployment tool shaft 204. To couple the two components, the cartridge 212 can be displaced to the right so that the locking pin 242 on the shaft 204 enters the axial slot 256 on the cartridge. The distal tip 216 can fit closely within the lumen 262 of the cartridge 212, and eventually the pin 242 can reach the end of the slot 256. The axial portion 248b of the L-shaped slot 246 on the shaft 204 can be aligned with the access port 270 on the cartridge 212, and thus travel over the segment of the flexible strip 222 of the suture snare 214 that extends diagonally through the distal end of the cartridge.

FIG. 13B shows the fastener cartridge being rotated or twisted in the clockwise direction relative to the shaft 204 so that the pin 242 travels along the circumferential slot 258 until it reaches the lockout 260. The pin 242 can be slightly wider than the slot 258, so that it "snaps" in to place within the lockout 260 as a tactile and audible indicator of full engagement. The circumferential portion 248a of the L-shaped slot 246 on the shaft 204 can accommodate the flexible strip 222 as the cartridge and shaft are relatively rotated. That is, the flexible strip 222 as well as the access port 270 on the cartridge 212 can eventually end up in registry with the side port 244 on the shaft 204 (see FIGS. 11C and 11E).

Figure 14A:
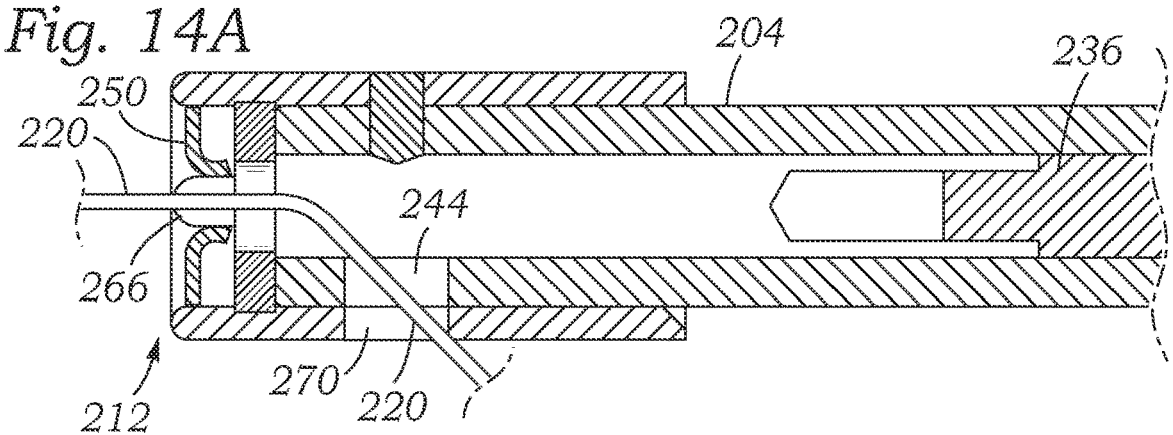
FIGS. 14A-14D are longitudinal sectional views through the disposable fastener cartridge on the end of the deployment tool illustrating steps in deploying the suture fastener.
Figure 14B:
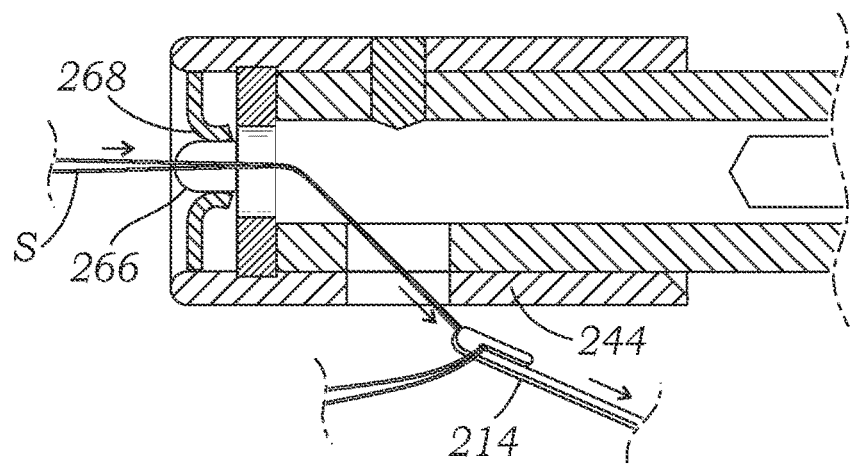

FIGS. 13A and 13B show placement of the flexible strip 222 of the suture snare 214 through the engaged components. More particularly, the strip 222 can extend radially inwardly through the access port 270 in the cartridge body 252, through the port 244 (see FIG. 11C) in the shaft 204, and then axially through the open fastener 250. This is also illustrated in FIG. 14A. Because of the L-shaped slots formed in both the shaft 204 and cartridge 212, the suture snare 214 can be ready to use once the two components are joined together. That is, the subassembly of the cartridge 212 and suture snare 214 can be pre-assembled and packaged in combination with a number of other subassemblies (e.g., packs of 6) for use with one of the delivery tools 200. By simply coupling each cartridge subassembly to the tool shaft 204, as explained above, the delivery system can be ready to install the suture fastener 250.

FIGS. 14A-14D are longitudinal sectional views through the disposable fastener cartridge 212 engaged with the end of the deployment tool 200, and illustrating steps in deploying the suture fastener 250. The assembly described above is first shown in FIG. 14A, which is the configuration just prior to introduction of the tool 200 to the implantation site for deployment of the fastener 250. The deployment sequence can also be understood with reference to FIGS. 15A-15B, which will be described in parallel.

Figure 15A:
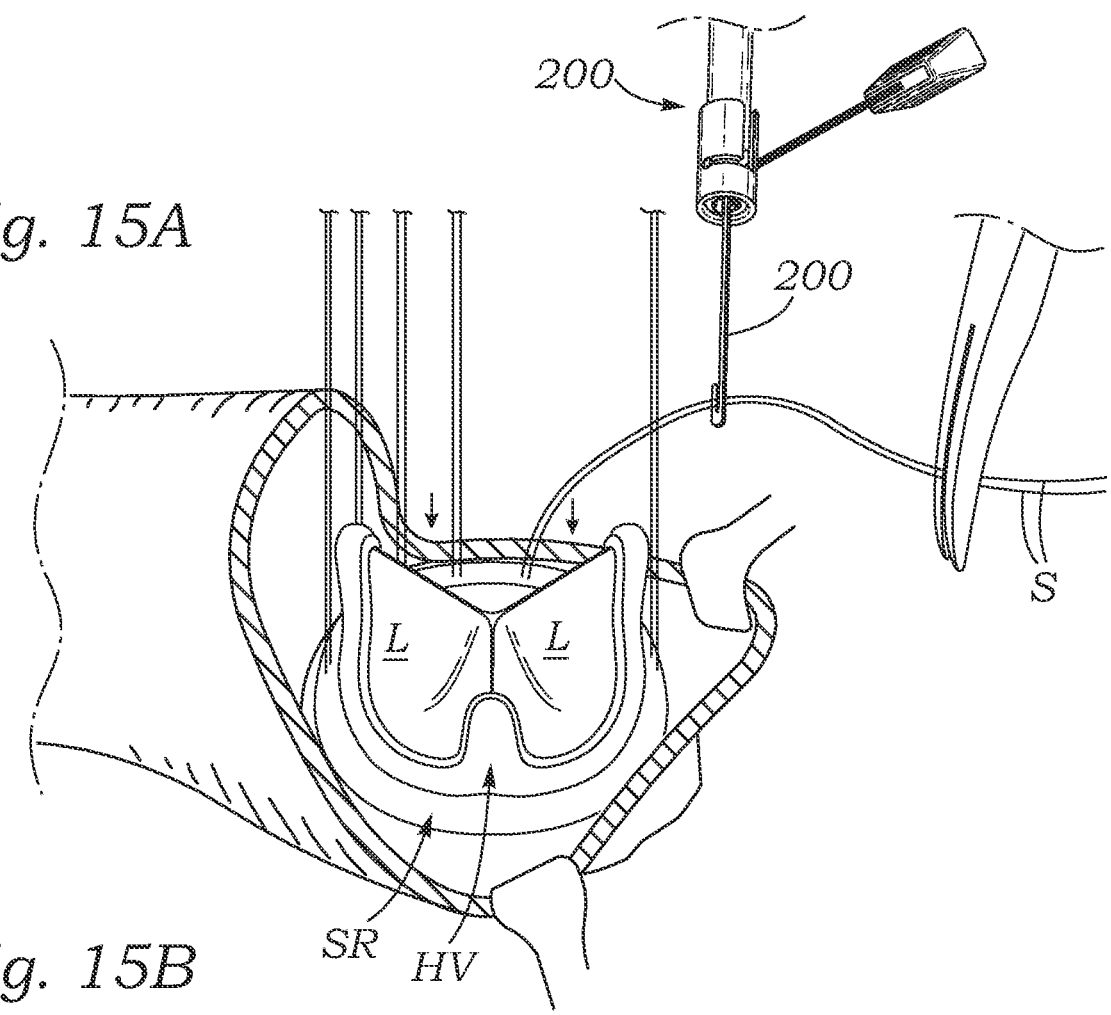
FIG. 15A is a perspective cutaway view of an aortic annulus showing a step in attachment of a surgical prosthetic heart valve using suture fasteners and a deployment tool of the present application.

FIG. 15A illustrates an ascending aorta opened up during a step in attachment of a surgical prosthetic heart valve HV to the aortic annulus using suture fasteners 250. The heart valve HV can be of a type having flexible leaflets L supported by commissure posts that extend in an outflow direction of the valve. The commissure posts can form a part of an internal support frame (not shown) typically covered by fabric. Secured around an inflow end of the support frame, a peripheral sewing ring SR can provide an anchoring zone for a plurality of anchoring sutures S that are pre-installed at the aortic annulus.

The surgeon can pre-attach the anchoring sutures S at evenly-spaced locations around the aortic annulus. The anchoring sutures S can be typically looped twice through the annulus from the outflow or ascending aorta side to the inflow or ventricular side. Of course, other suturing methods or pledgets may be used depending on surgeon preference. Once each anchoring suture S can be secured to the annulus, it can extend proximally in pairs of free lengths out of the operating site. The heart valve HV can be typically mounted on a valve holder and delivery handle (not shown), and the surgeon can thread the pairs of anchoring sutures S through evenly spaced locations around the sewing ring SR corresponding to their locations around the annulus. The surgeon then can advance the valve HV into position within the aortic annulus along the array of anchoring sutures S. Some of the anchoring sutures S are not shown around the front of the heart valve HV in FIG. 15A for clarity.

Subsequently, the surgeon can install a suture fastener 250 on each pair of anchoring sutures S on the proximal or outflow side of the sewing ring SR. This can be accomplished using the fastener deployment tool 200 in conjunction with the suture snare 214. First, the surgeon can capture two free lengths of a pair of anchoring sutures S with the snare end 220 of the snare 214 using forceps, for example. Subsequently, the surgeon can pull the suture snare 214 proximally through and out of engagement with the deployment tool 200, as indicated by the arrows in FIG. 14B. This can pull the anchoring sutures S through the suture fastener 250, through the internal channels of the cartridge 212 and deployment tool 200, and out of the side port 244.

Figure 14C:
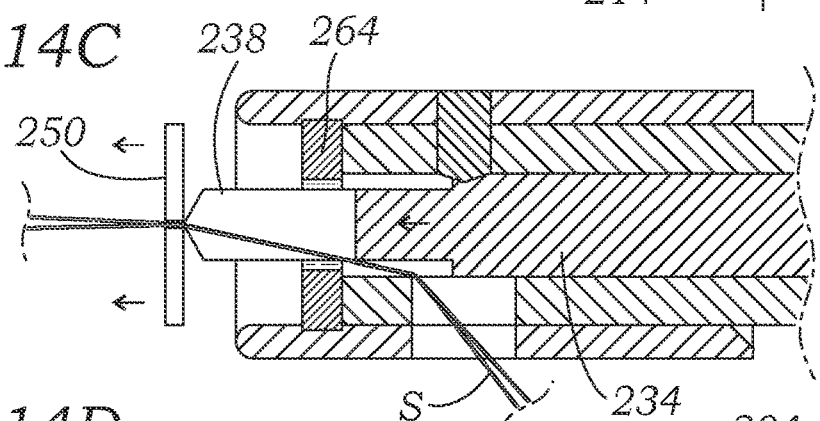

The surgeon then can maintain tension on the anchoring sutures S through the side port 244, and advance the shaft 204 of the deployment tool 200 distally until it contacts the valve sewing ring SR. The suture fastener 250 can then be deployed using the trigger actuator 206 (FIG. 9) on the deployment tool 200, as will be explained with reference to FIGS. 14C and 14D, so that it clamps down on the anchoring sutures S. The deployment tool 200 can then be retracted, and the anchoring sutures S severed just above the suture fastener 250, such as using scissors or a cutter integrated with the deployment tool. FIG. 15B shows a majority of the fasteners 250 already installed around the sewing ring SR to secure the heart valve HV to the aortic annulus.

After pulling the sutures S in a proximal direction through the fastener 250, cartridge 212, and deployment tool 200, the surgeon can trigger the actuator 206, which can displace the push rod 234 distally. As seen in FIG. 14C, the bifurcated fingers 238 at the distal end of the ejector 236 can eventually contact the inwardly bent tabs 268, and force the suture fastener 250 out of the cartridge 212. The fingers 238 can have a reduced diameter relative to the body of the ejector 236 so as to fit through the central opening of the annular rib 264. Furthermore, the bifurcated nature of the fingers 238 can provide a passageway for the sutures S, and prevent the fingers from binding the sutures, such as against the fastener 250.

Once the fastener 250 is pushed off of the stops 266, the biased tabs 268 can spring back toward their natural, relaxed shape (which, in the illustrated embodiment is in the plane of the rest of the fastener), clamping down on the sutures S. Assuming the surgeon has positioned the distal end of the cartridge 212 against the heart valve sewing ring SR, the fastener 250 can provide an anchor to hold the sewing ring against the annulus at that point.

Figure 14D:
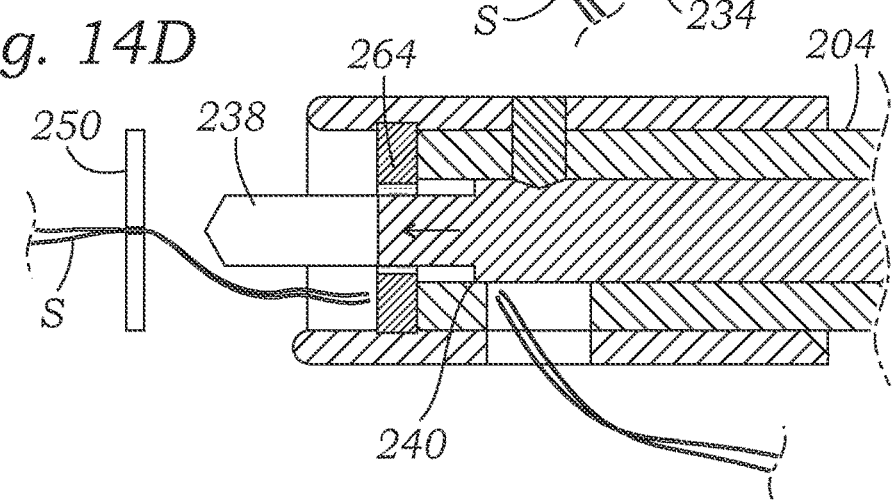
Figure 15B:
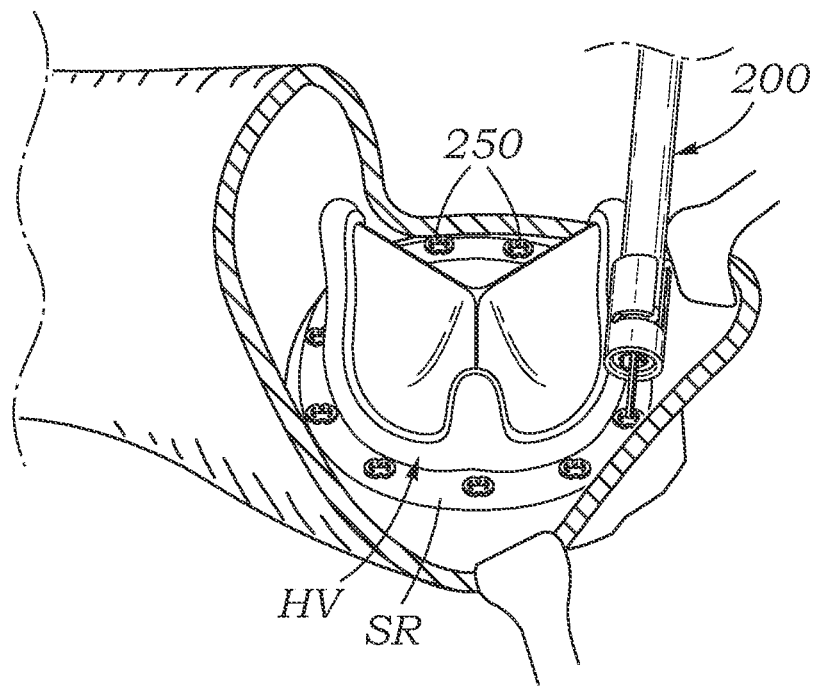
FIG. 15B is a view as in FIG. 15A showing a final step in attachment of the prosthetic heart valve with the suture fasteners and deployment tool.

Now with reference to FIG. 14D, further deployment of the actuator 206 and distal displacement of the push rod 234 can severs the sutures S. In particular, the sharp corner 240 on the ejector 236 can travel past the distal edge of the side port 244 in the deployment tool shaft 204. The side port 244 may also have a sharp corner, and the interaction between these two sharp corners can create a shearing action sufficient to sever the sutures S. Of course, this step may be omitted in favor of simply cutting sutures S close to the fastener 250 after removing the tool 200.

The heart valve HV can be representative of numerous types of heart valves, including those with flexible leaflets as shown, and also mechanical valves with rigid metallic leaflets, in addition to other surgical implants as mentioned above. Further, the flexible leaflet heart valve HV is shown with the suture fasteners 250 deployed from an outflow side of the valve, which typically indicates that the valve is for implant at the aortic annulus where the outflow is also the proximal side relative to conventional heart valve delivery. However, it should be understood that the suture fasteners 250 could be reversed within the heart valve HV so that they are deployed from the inflow side, such as in a mitral valve replacement procedure.

FIGS. 16A-16D illustrate an exemplary disposable fastener cartridge 212 with an alternative suture snare 300 during loading of the cartridge to a distal tip of the deployment tool and preparing the suture snare for use. Parts that are similar to those described above will be given the same number. In particular, the deployment tool can have an elongated tool shaft 204 that terminates in a distal tip 216 to which the cartridge 212 attaches.

Figure 16A:
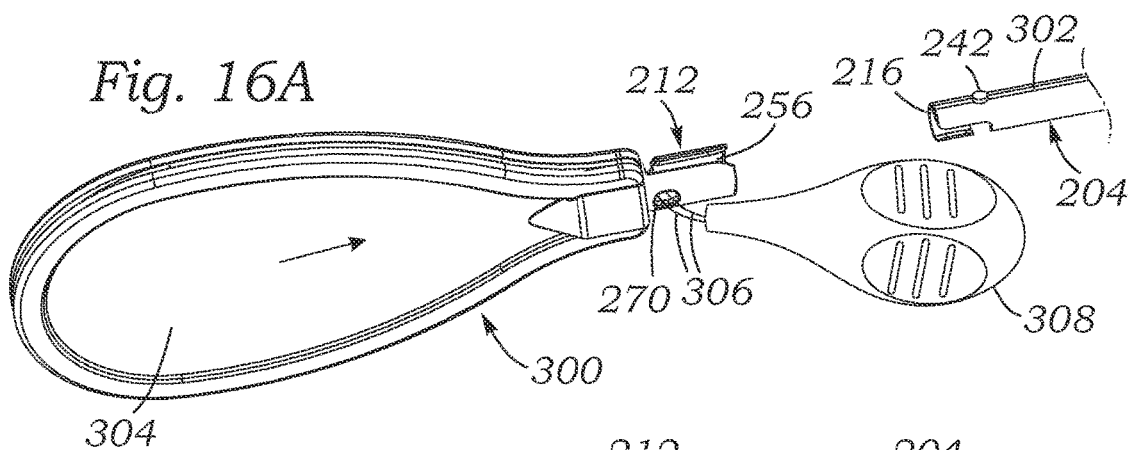
FIGS. 16A-16D illustrate several steps in loading an exemplary disposable fastener cartridge to a distal tip of the deployment tool and then preparing a suture snare for use.

In this embodiment, a marker line 302 can be provided on the same side of the tool shaft 204 as the locking pin 242 and extend a short distance from the distal tip 216 in a proximal direction. This marker line 302 can facilitate alignment of the axial slot 256 on the cartridge 212 with the locking pin 242. FIG. 16A shows relative displacement of the subassembly of the cartridge 212 and suture snare 300 toward the tool shaft 204. Eventually, as described above with respect to FIG. 13A, the locking pin 242 can reach the end of the axial slot 256.

Figure 16B:
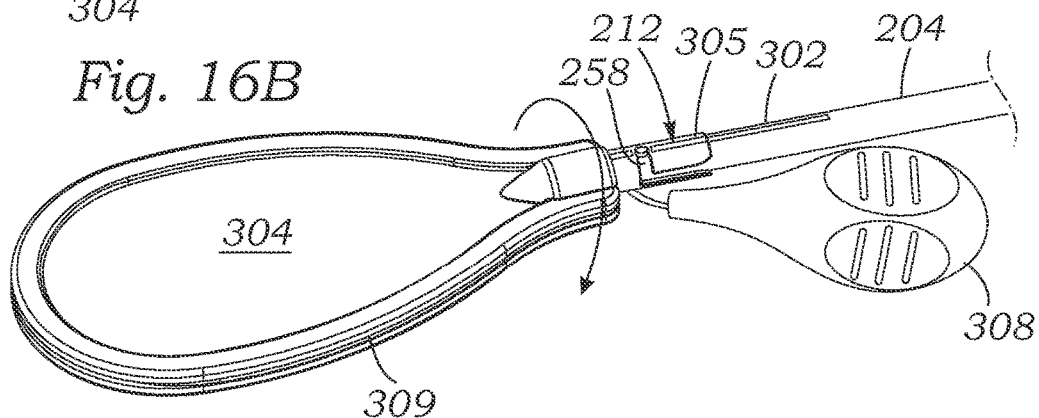

FIG. 16B shows 90° rotation, for example, clockwise, of a placement grip/key 304 of the suture snare 300 relative to the tool shaft 204. This can also rotate the fastener cartridge 212 relative to the shaft 204. As was explained above with respect to FIG. 13B, the locking pin 242 can travel along the circumferential slot 258 on the cartridge 212 until it reaches and snaps into the lockout 260 (best seen in FIG. 12A). An additional indicator of complete engagement can be the alignment of a second marker line 305 on the cartridge 212 with the marker line 302 on the shaft 204. At the same time, the circumferential portion 248a of the L-shaped slot 246 on the shaft 204 (see FIG. 11E) can accommodate two strands of a flexible snare wire 306 as the cartridge and shaft are relatively rotated.

The snare 300 can comprise the key 304, wire 306, and a proximal handle 308 in the form of a bulb. The flexible wire 306 can extend from the proximal handle 308 and loop around the placement grip/key 304, and can be held within an outer groove 309 therein. The loop formed by the wire 306 can be routed around the groove 309 in the placement grip/key 304 for shipping, storage and handling purposes, and to prevent twisting or tangling of the loop.

Figure 16C:
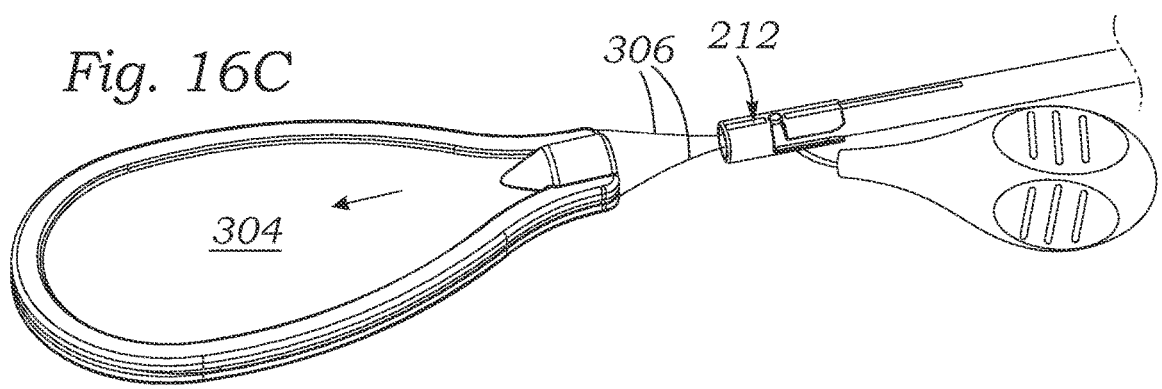
Figure 16D:
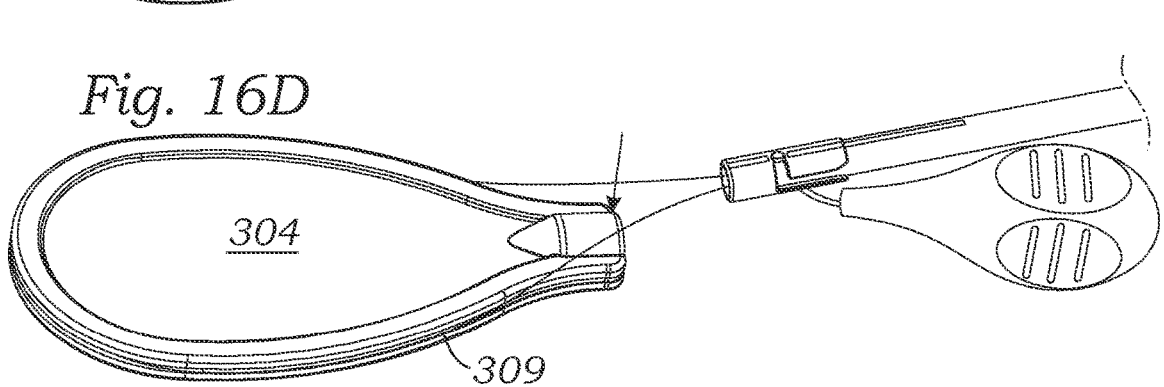

Subsequently, the user can pull the placement grip/key 304 axially away from the fastener cartridge 212 to create some separation therebetween, as seen in FIG. 16C. The two strands of the flexible wire 306 can thus be exposed. At this point, the placement grip/key 304 can be removed from within the loop of the flexible wire 306, for example, by pushing down on its proximal end, as seen in FIG. 16D. The suture fastener delivery system is now ready to use.

Figure 17A:
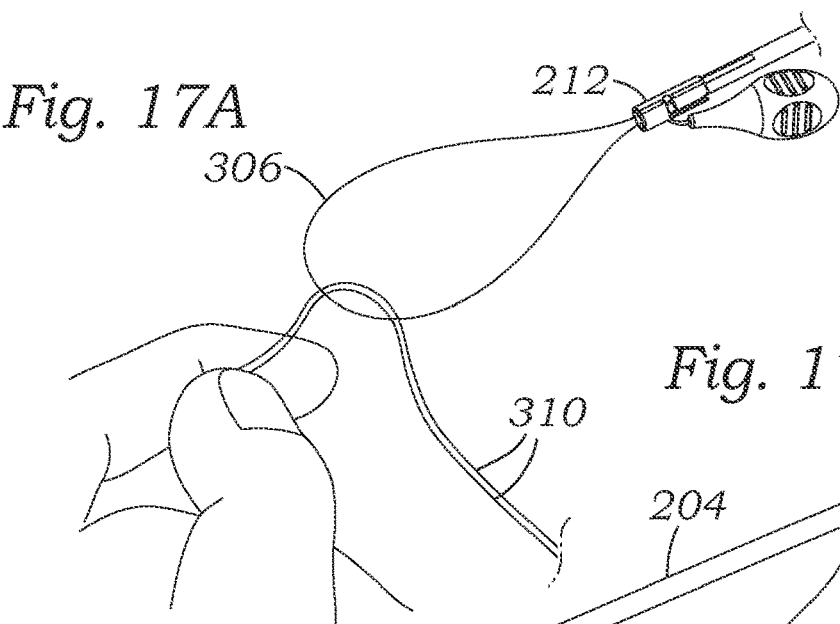

FIGS. 17A-17F show sequential steps in operation of the deployment tool 200 and fastener cartridge 212 during installation of a suture fastener 250 on the proximal side of an annuloplasty ring, such as the annuloplasty ring 2 shown in FIG. 1. FIG. 17A shows a technician passing one or more strands of sutures 310 through the loop of the flexible wire 306. In the illustrated embodiment, there are two strands of sutures 310 which represent a pre-installed suture that has been passed through a native heart valve annulus, and then through a peripheral sewing edge of the annuloplasty ring 2. A minimum length of the sutures 310 can be passed through the snare loop 306 to ensure that they remain captured while pulled through the cartridge 212, for example, about 5 cm.

Figure 17B:
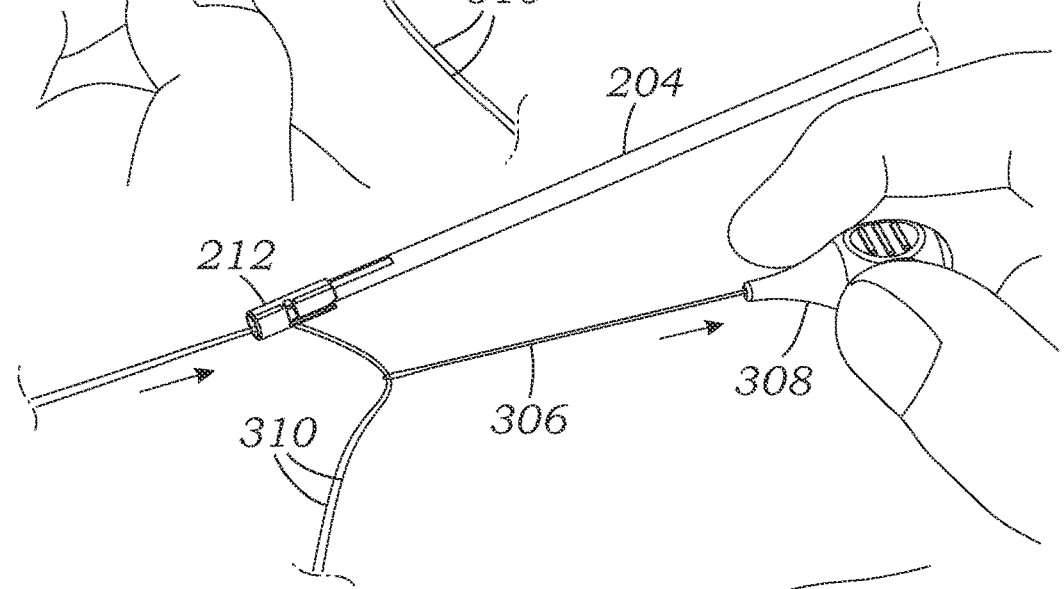
Figure 17C:
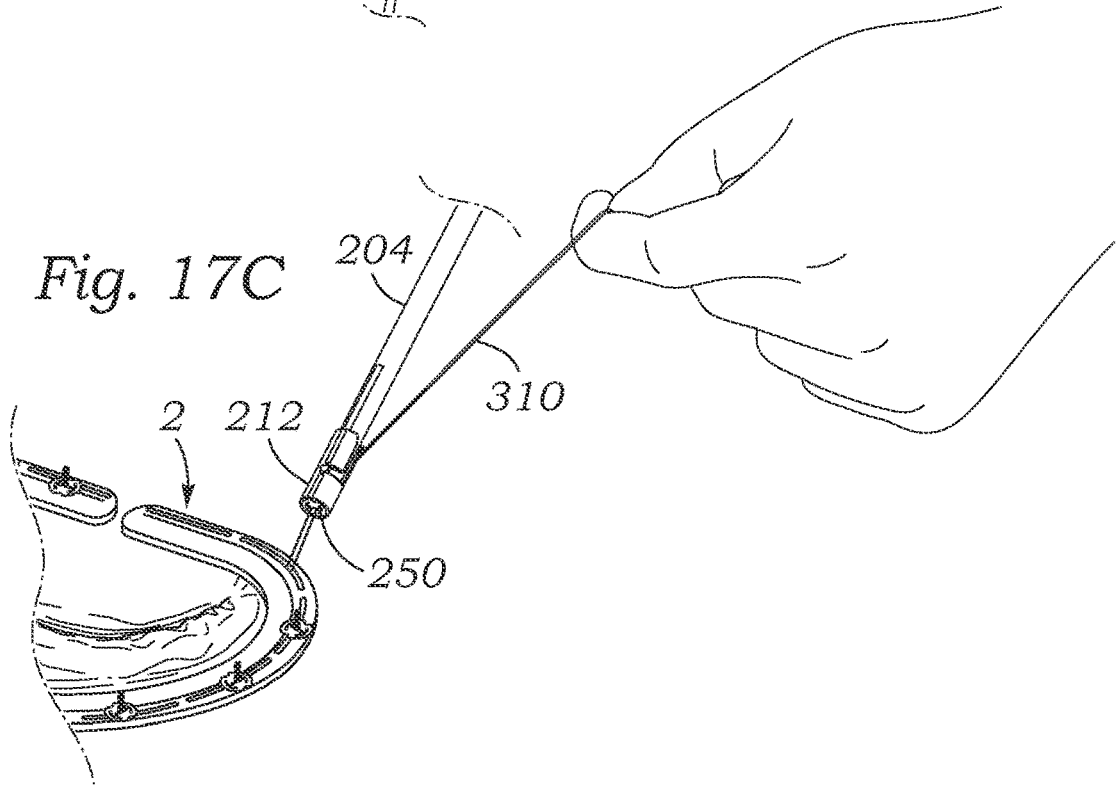

FIG. 17B illustrates the user pulling on the proximal handle 308, which in turn pulls the flexible wire loop 306 through the fastener cartridge 212, and also pulls the two strands of sutures 310 with it. The user can then grasp the sutures 310 with one of his or her hands, as seen in FIG. 17C, to place the sutures in tension through the ring 2 to the annulus.

As seen in FIG. 17D, the user can advance the distal tip of the shaft 204 having the cartridge 212 thereon down the sutures 310 to the target location on the annuloplasty ring 2. Only a portion of the annuloplasty ring 2 is shown, indicating that several suture fasteners 250 are already installed.

Finally, as seen in FIG. 17E, the user can actuate the delivery tool 200, such as by pulling the trigger actuator 206 as explained above, to deploy the suture fastener 250 and simultaneously cut the sutures 310. FIG. 17F is an enlargement of the installed suture fastener 250 showing short lengths of the sutures 310 remaining. At this stage, the fastener cartridge 212 can be removed from the shaft 204 to make way for another cartridge that has a suture fastener loaded therein.

FIGS. 18A-18C show steps for disengaging a used fastener cartridge 212 from the distal tip of the deployment tool shaft 204. Disengagement can be opposite from engagement, and involve rotating the cartridge 212 counterclockwise 900 in this example, and then pulling it axially free from the shaft 204. The deployment tool 200 can then be ready for coupling with another fastener cartridge. Engagement of a disposable fastener cartridge 212 and suture snare 300 with the tool shaft 204, application of the suture fastener 250 to the target location, and removal of the spent cartridge 212 from the tool shaft 204 can be done in a very short amount of time. Cycle times of less than a minute are possible. This can be significantly shorter than the time that it would take to tie off each of the sutures with a knot, especially in keyhole surgeries where space around the implant is limited.

FIG. 19 is a perspective cutaway view of the subassembly of the disposable fastener cartridge 212 and exemplary suture snare 300 of FIGS. 16A-16D. The fastener cartridge 212 has been described above, and will not be explained here other than to note that FIG. 20 is an exploded perspective view of the cartridge and a suture fastener 250.

As explained above, the suture snare 300 can comprise the placement grip/key 304 connected via the flexible wire 306 to the proximal handle 308. The placement grip/key 304 and proximal handle 308 can be made of a relatively soft polymer, such as an elastomer. A proximal end of the key 304 can include an enlarged annular sleeve 320 having an inner diameter that can be sized approximately the same as the outer diameter of the fastener cartridge 212. The annular sleeve 320 can thus be pushed over the distal tip of the cartridge 212 and it can be held thereon by a close interference fit.

The flexible wire 306 can pass inwardly through the aligned ports 270, 244, as explained above, out through the suture fastener 250 at the distal end of the cartridge 212, backward between the sleeve 320 and the cartridge, and then into the peripheral groove 309 around the key. The flexible wire 306 can be formed of an annealed stainless steel having a diameter of about 180 μm (about 0.007 inches), and can have sufficient flexibility to withstand kinking when routed in this manner.

Suture Fasteners Having Axially Spaced-Apart Layers

FIGS. 21A-21D illustrate another exemplary suture fastener 400. While certain suture fasteners disclosed herein (e.g., fasteners 30, 44, and 46 of FIGS. 3A-3D) can be solid throughout the thickness of their body, the fastener 400 can have a hollow portion such that the fastener defines multiple, axially spaced-apart layers through which suture may pass and be secured.

With reference to FIG. 21A, the suture fastener 400 can have a flat, generally disc-shaped body 404 segmented into two axially spaced-apart layers 408, 410 separated by a hollow or empty (e.g., devoid of material) portion 414 of the body. The hollow portion provides sufficient clearance to permit the tabs 434, 436 of the lower layer to move out of plane in the operation of the clip, as described above. The layers 408, 410 can be joined by common, contiguous annular edge segments 418, 420 of the body 404. With additional reference to FIG. 21B, annular, discontiguous sections between the common annular edge segments 418, 420 can define apertures to the hollow portion 414.

Each layer 408, 410 can include an outer annular edge 424 between inner 428 and outer 430 axial surfaces of the layers. As shown in FIG. 21C, each layer 408, 410 can include two tabs 434, 436 extending radially inwardly from its outer annular edge 424. The tabs 434, 436 can act as a clamping structure. The tabs 434, 436 of each layer 408, 410 can be separated from each other by a straight slit 440 that generally bifurcates an interior portion of the axial surfaces 428, 430. The opposing ends of the slit 440 can intersect curved slots 444, 446 that can extend proximate the perimeter of the outer annular edge 424 of each layer 408, 410. Each tab 434, 436 can thus be generally a half-circle, and the tabs and the middle slit 440 can form a generally H-shaped opening extending from the inner axial surface 428 and the outer axial surface 430, as shown in FIG. 21D.

Small circular enlargements 448 on the terminal end of each curved slot 444, 446 can facilitate bending of the tabs 434, 436, and can act as stress relievers to reduce the chance of fracture at those points. In some cases, the outer annular edges 424 of the layers 408, 410 can include semi-circular cutouts 452 on opposing radial surfaces. In particular examples, the cutouts 452 can be perpendicular to the slit 440. The cutouts 452 can provide an orientation feature for the suture fastener 400 to cooperate with features on a deployment device, such as a tool that can hold and deploy multiple suture fasteners in series. In other examples, the cutouts 452 can be located elsewhere on the fastener 400, the cutouts can be omitted, or another orienting feature used in addition to, or in place of, the cutouts.

Although the suture fastener 400 is shown with two axially spaced-apart layers 408, 410, in other cases, the suture fastener 400 can include more than two axially spaced-apart layers. Each of the axially spaced-apart layers may be separated by a hollow portion. Each layer can be configured in a similar manner in some aspects. In other aspects, one or more of the layers may have a different configuration. For example, the orientation of the slit 440, tabs 434, 436, slots 444, 446, or cutouts 452 may differ between layers, such that the suture openings of each of the axially spaced-apart layers are not axially, radially, or both axially and radially aligned.

In addition, a multi-layer suture fastener can comprise a clamping feature or structure other than that shown in FIGS. 21A-21D. In some cases, a multi-layer suture fastener can have a shape other than being disc-shaped or planar, such as having a curved shape, such as the shape of the fasteners 100 and 110 of FIGS. 5 and 6. The clamping or capture mechanism of the fastener may also differ from that shown in FIGS. 21A-21D. In some cases, one or more of the layers 408, 410 may include a slit that has a serpentine structure or surface features (such as ridges) that can aid in gripping suture. In further cases, the slit may have smooth or rounded edges, such as to reduce the chance of inadvertently severing or damaging suture. In various examples, a multi-layer suture fastener can have a different type of clamping structure, such as the clamping features of the suture fasteners of any of FIG. 3A-3D, 4A-4D, or 5-8, or of the suture fasteners disclosed in U.S. Patent Application Publication No. 2014/0031864A1 or U.S. Patent Application Publication No. 2016/0183937A1, each of which is incorporated by reference herein in its entirety.

The suture fastener 400 can be constructed generally as described for the suture fasteners shown in FIGS. 3A-3D, including being made from elastic or superelastic materials. The suture fastener 400 can also operate in a similar manner, such as having a capture mechanism (the tabs 434, 436 and the slit 440) that can be elastically deformed to an open position to receive one or more lines of suture and then resume a closed position whereby the suture is retained and secured against longitudinal (or lateral) movement relative to the suture fastener 400. In other cases, a multi-layer suture fastener can be made from a plastically-deformable material, one or more lines of suture can be inserted through an opening in the fastener, and the fastener can be crimped or compressed such that the opening collapses, and the lines of suture are secured against longitudinal (or lateral) movement relative to the suture fastener.

The use of suture fasteners having multiple axially spaced-apart layers 408, 410 can provide a number of advantages. For example, one or more lines of suture extending through the fastener 410 can be gripped between the slits 440 of each of the layers 408, 410. Thus, being gripped by multiple slits, the suture can be gripped more securely than in at least some examples of a suture fastener having a single slit or other retaining mechanism. Applying a plurality single-layer suture fasteners of the type described above to a single suture can be difficult because the system automatically cuts the suture (310, FIGS. 17D and 17F) to provide a short tail, which can make applying the second fastener challenging.

In addition, one or more of the layers 408, 410 can have a thickness less than the thickness of a unitary suture fastener (such as the suture fasteners of FIGS. 3A-3D). In some cases, the use of multiple thinner layers, such as the layers 408, 410, can allow the overall thickness of the suture fastener 400 to be thinner than a unitary (e.g., single-layer) suture fastener. For example, the use of multiple layers can allow the suture fastener to provide a stronger securing force than a unitary suture fastener of equivalent overall thickness. In addition, layers having a thinner thickness that the thickness of an overall suture fastener can allow a suture to be severed more closely to the surface of a layer 408, 410 of the fastener 400, which can produce shorter suture tail lengths after the fastener has been deployed. Shorter suture tail lengths can, for example, expedite the healing process and improve surgical outcomes.

In some embodiments, the suture fastener 400 can be deployed at least generally as described for the fasteners 30, 44, and 46 of FIGS. 3A-3D, including using the fastener deployment tool 200 and suture snare 224 of FIGS. 9-20. In further embodiments, the suture fastener can be deployed using a deployment tool that can hold and deploy multiple fasteners in series, such as described in U.S. Patent Application Publication No. 2016/0183937A1, incorporated by reference herein in its entirety. In other cases, the suture fastener 400 can be deployed in a different manner.

GENERAL CONSIDERATIONS

For purposes of this description, certain aspects, advantages, and novel features of the embodiments of this disclosure are described herein. The disclosed methods, apparatuses, and systems should not be construed as limiting in anyway. Instead, the present disclosure is directed toward all novel and nonobvious features and aspects of the various disclosed embodiments, alone and in various combinations and sub-combinations with one another. The methods, apparatuses, and systems are not limited to any specific aspect or feature or combination thereof, nor do the disclosed embodiments require that any one or more specific advantages be present or problems be solved.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

Although the operations of some of the disclosed methods are described in a particular, sequential order for convenient presentation, it should be understood that this manner of description encompasses rearrangement, unless a particular ordering is required by specific language. For example, operations described sequentially may in some cases be rearranged or performed concurrently. Moreover, for the sake of simplicity, the attached figures may not show the various ways in which the disclosed methods can be used in conjunction with other methods. As used herein, the terms "a", "an", and "at least one" encompass one or more of the specified element. That is, if two of a particular element are present, one of these elements is also present and thus "an" element is present. The terms "a plurality of" and "plural" mean two or more of the specified element.

As used herein, the term "and/or" used between the last two of a list of elements means any one or more of the listed elements. For example, the phrase "A, B, and/or C" means "A", "B,", "C", "A and B", "A and C", "B and C", or "A, B, and C."

As used herein, the term "coupled" generally means physically coupled or linked and does not exclude the presence of intermediate elements between the coupled items absent specific contrary language.

In view of the many possible embodiments to which the principles of the disclosure may be applied, it should be recognized that the illustrated embodiments are only preferred examples and should not be taken as limiting the scope of the disclosure. Rather, the scope of the disclosure is at least as broad as the following claims. I therefore claim all that comes within the scope of the following claims.

What is claimed is:

1. A device for securing one or more lines of suture, comprising:
    a generally disc-shaped body defining a plurality of axially spaced-apart layers, each axially spaced-apart layer of the plurality of axially spaced-apart layers comprising:
        an outer axial surface;
        an inner axial surface, wherein the inner axial surfaces of the plurality of axially spaced-apart layers define a hollow interior portion of the generally disc-shaped body;
        an opening extending through an axial surface of at least one axially spaced-apart layer of the plurality of axially spaced-apart layers, the opening defining a first edge in the at least one axially spaced-apart layer and a second edge in the at least one axially spaced-apart layer, the opening being a suture opening providing access to the hollow interior portion, wherein the first edge and the second edge are elastically deformable from a closed configuration to an open configuration such that the first edge and the second edge resume the closed configuration once a biasing force is removed from the at least one axially spaced-apart layer, wherein the first edge and the second edge are spaced apart by a first distance when in the open configuration and a second distance when in the closed configuration, the second distance being smaller than the first distance; and
    wherein one or more lines of suture can be passed through the opening when the first edge and the second edge are in the open configuration and the one or more lines of suture are restricted by the first edge and the second edge from sliding through the suture opening in at least one longitudinal direction of the one or more lines of suture when the first edge and the second edge are in the closed configuration.

2. The device of claim 1, wherein the first edge and the second edge are biased toward the closed configuration.

3. The device of claim 1, wherein the suture opening is a first suture opening and is axially aligned with a second suture opening formed in at least another axially spaced-apart layer of the plurality of axially spaced-apart layers.

4. The device of claim 1, wherein the first edge and the second edge form respective edges of first and second tabs defined in the axial surface of the at least one axially spaced-apart layer.

5. The device of claim 4, wherein the opening is axially and radially aligned with an opening of at least another axially spaced-apart layer of the plurality of axially spaced-apart layers.

6. The device of claim 1, the generally disc-shaped body further defining:

an aperture extending circumferentially about at least a first portion of an outer radial surface of the generally disc-shaped body and continuous with the hollow interior portion.

7. The device of claim 6, wherein at least a first portion of the outer radial surface defines an axially contiguous edge segment.

8. The device of claim 7, wherein at least a second portion of the outer radial surface is not axially contiguous.

9. The device of claim 8, wherein the at least a second portion of the outer radial surface defines an aperture to the hollow interior portion.

10. The device of claim 1, wherein the device consists of two axially spaced-apart layers.

11. The device of claim 1, wherein the device comprises more than two axially spaced-apart layers.

12. A method for securing one or more lines of suture, the method comprising:
placing one or more lines of suture at an anatomical location;
placing a suture fastener at the anatomical location, the suture fastener comprising:
a generally disc-shaped body defining a plurality of axially spaced-apart layers, each axially spaced-apart layer of the plurality of axially spaced-apart layers comprising:
an outer axial surface;
an inner axial surface, wherein the inner axial surfaces of the plurality of axially spaced-apart layers define a hollow interior portion of the generally disc-shaped body;
an opening extending through an axial surface of at least one axially spaced-apart layer of the plurality of axially spaced-apart layers, the opening defining a first edge in the at least one axially spaced-apart layer and a second edge in the at least one axially spaced-apart layer, the opening being a suture opening providing access to the hollow interior portion, wherein the first edge and the second edge are elastically deformable from a closed configuration to an open configuration such that the first edge and the second edge resume the closed configuration once a biasing force is removed from the at least one axially spaced-apart layer, wherein the first edge and the second edge are spaced apart by a first distance when in the open configuration and a second distance when in the closed configuration, the second distance being smaller than the first distance; and
wherein one or more lines of suture can be passed through the opening when the first edge and the second edge are in the open configuration and the one or more lines of suture are restricted by the first edge and the second edge from sliding through the suture opening in at least one longitudinal direction of the one or more lines of suture when the first edge and the second edge are in the closed configuration;
applying a force to the suture fastener to place the first edge and the second edge in the open configuration, wherein, when in the open configuration, the one or more lines of suture may freely move through the opening;
passing the one or more lines of suture through the opening while the first edge and the second edge are placed in the open configuration; and
removing the force to allow the first edge and the second edge to resume the closed configuration, wherein, when in the closed configuration, the first edge and the second edge engage the one or more lines of suture such that the one or more lines of suture resist movement relative to the opening in either longitudinal direction of the one or more lines of suture.

13. The method of claim 12, wherein placing the first edge and the second edge in the closed configuration comprises compressing the suture fastener such that at least a portion of the suture fastener plastically deforms.

14. The method of claim 12, wherein the first edge and the second edge are biased toward the closed configuration.

15. The method of claim 12, wherein placing the first edge and the second edge in the open configuration comprises elastically deforming the first edge and the second edge during deployment and wherein the first edge and the second edge elastically resume the closed configuration after deployment of the suture fastener about the one or more lines of suture.

16. The method of claim 12, wherein the plurality of axially spaced-apart layers consists of two axially spaced-apart layers.

17. The method of claim 12, wherein the suture opening is a first suture opening and is axially aligned with a second suture opening formed in at least another axially spaced-apart layer of the plurality of axially spaced-apart layers.

18. A suture fastener deployment system, comprising:
a deployment device comprising a handle, a shaft extending from the handle; and
a suture fastener comprising:
a generally disc-shaped body defining a plurality of axially spaced-apart layers, each axially spaced-apart layer of the plurality of axially spaced-apart layers comprising:
an outer axial surface;
an inner axial surface, wherein the inner axial surfaces of the plurality of axially spaced-apart layers define a hollow interior portion of the generally disc-shaped body;
an opening extending through an axial surface of at least one axially spaced-apart layer of the plurality of axially spaced-apart layers, the opening defining a first edge in the at least one axially spaced-apart layer and a second edge in the at least one axially spaced-apart layer, the opening being a suture opening providing access to the hollow interior portion, wherein the first edge and the second edge are elastically deformable from a closed configuration to an open configuration such that the first edge and the second edge resume the closed configuration once a biasing force is removed from the at least one axially spaced-apart layer, wherein the first edge and the second edge are spaced apart by a first distance when in the open configuration and a second distance when in the closed configuration, the second distance being smaller than the first distance; and
wherein one or more lines of suture can be passed through the opening when the first edge and the second edge are in the open configuration and the one or more lines of suture are restricted by the first edge and the second edge from sliding through the suture opening in at least one longitudinal direction of the one or more lines of suture when the first edge and the second edge are in the closed configuration.

19. The suture fastener deployment system of claim 18, wherein the first edge and the second edge are biased toward the closed configuration.

20. The suture fastener deployment system of claim 18, wherein the fastener deployment system is configured to elastically deform the first edge and the second edge to the open configuration during deployment, and the first edge and the second edge elastically resume the closed configuration after deployment of the suture fastener and, while in the open configuration, the one or more lines of suture have been inserted through the suture opening.

\* \* \* \* \*